US008541557B2

(12) United States Patent
Ohta

(10) Patent No.: US 8,541,557 B2
(45) Date of Patent: Sep. 24, 2013

(54) AZO COMPOUND AND METHOD OF PREPARING THE AZO COMPOUND

(75) Inventor: Masafumi Ohta, Susoso (JP)

(73) Assignee: Ricoh Company, Ltd., Tokyo (JP)

( * ) Notice: Subject to any disclaimer, the term of this patent is extended or adjusted under 35 U.S.C. 154(b) by 0 days.

(21) Appl. No.: 13/524,664

(22) Filed: Jun. 15, 2012

(65) Prior Publication Data

US 2012/0253025 A1     Oct. 4, 2012

Related U.S. Application Data

(62) Division of application No. 12/146,734, filed on Jun. 26, 2008, now Pat. No. 8,232,376.

(30) Foreign Application Priority Data

Jun. 29, 2007 (JP) ................................. 2007-172269
Sep. 11, 2007 (JP) ................................. 2007-235747

(51) Int. Cl.
| *C09B 35/34* | (2006.01) |
| *C09B 35/378* | (2006.01) |
| *C09B 35/04* | (2006.01) |
| *C09B 56/00* | (2006.01) |
| *C09B 56/12* | (2006.01) |
| *C09B 56/06* | (2006.01) |

(52) U.S. Cl.
USPC ........... 534/654; 534/689; 534/759; 534/658; 534/797; 534/755; 534/812; 534/691; 534/829

(58) Field of Classification Search
USPC ................................................. 534/654, 689
See application file for complete search history.

(56) References Cited

U.S. PATENT DOCUMENTS

| 3,262,924 A | 7/1966 | Green |
| 3,654,260 A | 4/1972 | Tsuchida |
| 3,913,143 A | 10/1975 | Schneider et al. |
| 3,931,143 A | 1/1976 | MacLeay et al. |
| 4,206,115 A | 6/1980 | Idelson |
| 4,242,260 A | 12/1980 | Sasaki et al. |
| 4,251,613 A | 2/1981 | Sasaki et al. |
| 4,272,598 A | 6/1981 | Sasaki et al. |
| 4,279,981 A | 7/1981 | Ohta et al. |
| 4,314,015 A | 2/1982 | Hashimoto et al. |
| 4,396,696 A | 8/1983 | Nagasaka et al. |
| 4,440,845 A | 4/1984 | Hashimoto |
| 4,537,844 A | 8/1985 | Hashimoto |
| 4,555,567 A | 11/1985 | Hashimoto |
| 4,596,754 A | 6/1986 | Tsutsui et al. |
| 4,605,697 A | 8/1986 | Gerbal et al. |
| 4,656,257 A | 4/1987 | Hashimoto |
| 5,317,093 A | 5/1994 | Hashimoto |
| 5,416,211 A | 5/1995 | Barnett et al. |
| 5,612,482 A | 3/1997 | Barnett et al. |
| 5,644,058 A | 7/1997 | Barnett et al. |
| 5,663,339 A | 9/1997 | Barnett et al. |
| 5,892,034 A | 4/1999 | Barnett et al. |
| 6,005,085 A | 12/1999 | Ueno et al. |
| 6,132,914 A | 10/2000 | Shimada |
| 6,646,111 B1 | 11/2003 | Carlini et al. |
| 8,232,376 B2 * | 7/2012 | Ohta ............................ 534/658 |
| 2004/0161691 A1 | 8/2004 | Ogawa et al. |
| 2005/0182247 A1 | 8/2005 | Tzikas et al. |
| 2006/0240354 A1 | 10/2006 | Ohtani |
| 2008/0161545 A1 | 7/2008 | Egli et al. |

FOREIGN PATENT DOCUMENTS

| CN | 1521563 A | | 8/2004 |
| DE | 3221642 A | * | 1/1983 |
| DE | 19718523 A1 | | 11/1998 |
| EP | 0457334 A1 | | 11/1991 |
| EP | 0913430 A1 | | 5/1999 |
| EP | 1840172 A2 | | 10/2007 |
| JP | 53-133229 | | 11/1978 |
| JP | 54-12742 | | 1/1979 |
| JP | 57-202349 | | 12/1982 |
| JP | 59-66460 | | 4/1984 |
| JP | 59-75964 | | 4/1984 |
| JP | 59-127050 | | 7/1984 |
| JP | 59-217764 | | 12/1984 |
| JP | 60-215081 | | 10/1985 |
| JP | 60-230151 | | 11/1985 |
| JP | 62-11862 | | 1/1987 |
| JP | 63-56574 | | 3/1988 |
| JP | 63-301054 | | 12/1988 |
| JP | 1-229263 | | 9/1989 |
| JP | 1-234856 | | 9/1989 |
| JP | 2-110569 | | 4/1990 |

(Continued)

OTHER PUBLICATIONS

Oct. 6, 2008 search report in connection with a counterpart European patent application No. 08 15 9108.

Al-Kassim, Salwa, et al., "Communications New Intermediates and Dyes for Synthetic-polymer Fibres", *Journal of the Society of Dyers and Colourists*, Society of Dyers and Colourists, Bradford, GB, vol. 89, Jan. 1, 1973 p. 359.

Nagasaki, Takeshi, et al., "Photochemically size-controllable dendrimers including a 1,3-Alternate calyx[4]arene as a core and azabenzene moieties as branches" *Anales de Quinmica Int. Ed.* vol. 93, 1997, pp. 341-346.

(Continued)

*Primary Examiner* — Yong Chu
(74) *Attorney, Agent, or Firm* — Cooper & Dunham LLP

(57) ABSTRACT

An azo compound having the following formula (I):

$$A(E)n \qquad (I)$$

wherein A represents a residue of an azo compound, bonded with n pieces of E group through one or more heteroatom being N or O and forming a part of the residue A; E independently represents a hydrogen atom or —C(=O)—O—R1 wherein R1 represents a substituted or an unsubstituted alkyl group having 4 to 10 carbon atoms, an alkenyl group, an alkynyl group, a cycloalkyl group, a cycloalkenyl group or an aralkyl group; and n represents an integer of from 1 to 10.

1 Claim, No Drawings

(56) References Cited

FOREIGN PATENT DOCUMENTS

| | | |
|---|---|---|
| JP | 3-7945 | 1/1991 |
| JP | 4-117464 | 4/1992 |
| JP | 4-204741 | 7/1992 |
| JP | 4-212968 | 8/1992 |
| JP | 4-229868 | 8/1992 |
| JP | 4-229869 | 8/1992 |
| JP | 5-32906 | 2/1993 |
| JP | 5-158263 | 6/1993 |
| JP | 5-249714 | 9/1993 |
| JP | 7-181692 | 7/1995 |
| JP | 8-15888 | 1/1996 |
| JP | 10-20528 | 1/1998 |
| JP | 10-153869 | 6/1998 |
| JP | 10-239880 | 9/1998 |
| JP | 2000-75522 | 3/2000 |
| JP | 2000-75523 | 3/2000 |
| JP | 2000-137339 | 5/2000 |
| JP | 2000-171991 | 6/2000 |
| JP | 2000-231208 | 8/2000 |
| JP | 2001-207115 | 7/2001 |
| JP | 2004-78148 | 3/2004 |
| JP | 2005-24929 | 1/2005 |
| JP | 2008-101154 | 5/2008 |
| WO | WO98/32802 | 7/1998 |
| WO | WO03/102083 A1 | 12/2003 |
| WO | WO2005/054375 A1 | 6/2005 |
| WO | WO2006/061438 A1 | 6/2006 |

OTHER PUBLICATIONS

Sokolova, N.B., et al., "Photodegradation of Azo Dyes with heterocyclic and Benzene Groups In Polymeric Matrix", *Russian Journal of Applied Chemistry*, Pleiades Publishing / Springer, New York, NY, US, vol. 75, No. 2, Jan. 1, 2002, pp. 254-256.

Towns, A.D., "Developments in azo disperse dyes derived from heterocyclic diazo components", *Dyes and Pigments*, vol. 42, 1999, pp. 3-28.

Wamhoff, Heinrich "Zur Reaktion von 2-Amino-3athozycarbonyl-4.5-dihydrofuranen mit Phenylazid und Benz-phenylhydrazid-chlorid" *Chemische Berichte*, vol. 104, 1971, pp. 3510-3518.

Apr. 8, 2009 European search report in connection with a counterpart European patent application No. 08 15 9108.

Heppke, G., et al., "Colored and Black Liquid Crystalline Mixtures with new Anthraquinone Dyes", *Mol. Cryst. Liq. Cryst.* 1983, pp. 191-204, vol. 94, Gordon and Breach Science Publishers, Inc., U.S.A.

Khalifa, M. E., et al., "Physicochemical Studies on the Complexation of Indium (III) with Tris-[4-[(3'-carboxy-4'-hydroxy)phenylazo]phenyl] amine ($H_3$ TPAPA)", *Bulletin de la Société Chimique de France*, 1988, pp. 967-969, No. 6.

Leslie, T. M., et al., "The Synthesis and Characterization of Some Perylene and Anthra-Quinoic Dichroic Dyes for Liquid Crystal Display Applications", *Liquid Crystals and Ordered Fluids*, 1984, pp. 43-55, vol. 4, Plenum Press.

Takahashi, Toru, et al., "Surface Relief Grating Formation Using a Novel Azobenzene-based Photochromic Amorphous Molecular Material, Tris[4-(phenylazo)phenyl]amine", *Mol. Cryst. Liq. Cryst.* 2005, pp. 9-14, vol. 430, Taylor & Francis, Inc.

Oct. 13, 2010 European official action in connection with counterpart European patent application No. 08159108.

Sep. 16, 2011 Chinese official action in connection with a counterpart Chinese patent application.

* cited by examiner

AZO COMPOUND AND METHOD OF PREPARING THE AZO COMPOUND

CROSS-REFERENCE TO RELATED APPLICATIONS

This application is a divisional of U.S. application Ser. No. 12/146,734, filed Jun. 26, 2008 (now U.S. Pat. No. 8,232,376), which claims the priority of Japanese Patent Applications Nos. 2007-172269 and 2007-235747, filed with the Japanese Patent Office on Jun. 29, 2007 and Sep. 11, 2007, respectively.

BACKGROUND OF THE INVENTION

1. Field of the Invention

The present invention relates to an azo compound used as an organic photoconductive material, and to a method of preparing the azo compound.

2. Discussion of the Related Art

Conventionally, an azo compound has been used as an organic photoconductive material, particularly as a charge generation pigment in a multilayered photoreceptor being an embodiment of electrophotographic photoreceptors.

The multilayered photoreceptor is known to be a photoreceptor including an electroconductive substrate; a charge generation layer formed on the electroconductive substrate, including a charge generation pigment having charge generatability as a main component; and a charge transport layer formed on the charge generation layer, efficiently absorbing a charge generated by the charge generation layer and including a charge transport material capable of transporting the charge as a main component. Conventionally, as azo compounds for use in such photoreceptors, Japanese published unexamined applications Nos. 47-37543 and 52-55643 disclose benzidine bisazo compounds; Japanese published unexamined application No. 52-8832 discloses stilbene bisazo compounds; Japanese published unexamined application No. 58-222152 discloses diphenylhexatriene bisazo compounds; and Japanese published unexamined application No. 58-222153 discloses diphenylbutadiene bisazo compounds.

However, the multilayered photoreceptor using a conventional azo compound typically has low sensitivity, which is unsatisfactory to a photoreceptor for high-speed copiers. One of the reasons is thought that impurities are not fully removed from the azo compound because the azo compound typically has very low solubility with an organic solvent and is purified only by being washed with an organic solvent. In addition, a combination with a long-time dispersion process by methods such as a ball milling method to prepare a dispersion liquid in which microscopic particles are uniformly dispersed or a use of a resin dispersion stabilizer is inevitable.

Because of these reasons, a need exists for an azo compound useful as an organic photoconductive material, overcoming the conventional drawbacks.

SUMMARY OF THE INVENTION

Accordingly, an object of the present invention is to provide an azo compound having good solubility in an organic solvent, which is useful as an organic photoconductive material used for high-sensitive electrophotographic photoreceptors, particularly for multilayered photoreceptors, practicable for not only high-speed copiers but also laser printers.

Another object of the present invention is to provide a method of preparing the azo compound.

To achieve such objects, the present invention contemplates the provision of an azo compound having the following formula (I):

$$A(E)n \qquad (I)$$

wherein A represents a residue of an azo compound, bonded with n pieces of E group through one or more heteroatom being N or O and forming a part of the residue A; E independently represents a hydrogen atom or —C(=O)—O—R1 wherein R1 represents a substituted or an unsubstituted alkyl group having 4 to 10 carbon atoms, an alkenyl group, an alkynyl group, a cycloalkyl group, a cycloalkenyl group or an aralkyl group; and n represents an integer of from 1 to 10.

DESCRIPTION OF THE PREFERRED EMBODIMENTS

Generally, the present invention provides an azo compound useful as an organic photoconductive material used for high-sensitive electrophotographic photoreceptors for high-speed copiers.

More particularly, the present invention relates to an azo compound having the following formula (I):

$$A(E)n \qquad (I)$$

wherein A represents a residue of an azo compound, bonded with n pieces of E group through one or more heteroatom being N or O and forming a part of the residue A; E independently represents a hydrogen atom or —C(=O)—O—R1 wherein R1 represents a substituted or an unsubstituted alkyl group having 4 to 10 carbon atoms, an alkenyl group, an alkynyl group, a cycloalkyl group, a cycloalkenyl group or an aralkyl group; and n represents an integer of from 1 to 10.

The residue A is preferably a residue of a compound having the following formula (II):

$$B—(N=N-Cp)m \qquad (II)$$

wherein B represents a main backbone of an azo compound; Cp represents a coupler component residue; and m represents an integer of 2 or 3.

The coupler component residue is preferably a member selected from the group consisting of aromatic hydrocarbon compound residues having a hydroxyl group, heterocyclic compound residues having a hydroxyl group, aromatic hydrocarbon compound residues having an amino group, heterocyclic compound residues having an amino group, aromatic hydrocarbon compound residues having a hydroxyl group and an amino group, heterocyclic compound residues having a hydroxyl group and an amino group, and compound residues having an aliphatic or an aromatic enolic ketone group.

The aromatic hydrocarbon compound residue having a hydroxyl group is preferably a member selected from the group consisting of phenolic compound residues and naphthol compound residues, and the aromatic hydrocarbon compound residues having a hydroxyl group and an amino group are preferably aminonaphthol compounds.

The Cp is preferably at least any one of compounds having the following formulae (5) to (13):

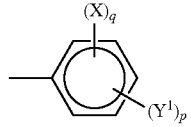

(5)

-continued (6)

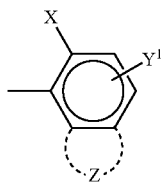

(7)

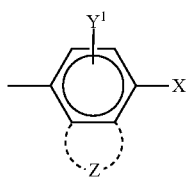

(8)

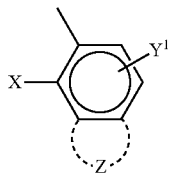

wherein X represents —OH, —N(R$^1$)(R$^2$) or —NHSO$_2$—R$^3$ wherein R$^1$ and R$^2$ independently represents a hydrogen atom or a substituted or an unsubstituted alkyl group, and R3 represents a substituted or an unsubstituted alkyl group or a substituted or an unsubstituted aryl group; Y$^1$ represents a hydrogen atom, a halogen atom, a substituted or an unsubstituted alkyl group, a substituted or an unsubstituted alkoxy group, a carboxy group, a sulfone group, a substituted or an unsubstituted sulfamoyl group or —CON(R$^4$)(Y$^2$) wherein R$^4$ represents an alkyl group or its substituents, or a phenyl group or its substituents, and Y$^2$ represents a ring hydrocarbon group or its substituents, a heterocyclic group or its substituents, or —N=C(R$^5$)(R$^6$) wherein R$^5$ represents a ring hydrocarbon group or its substituents, a heterocyclic group or its substituents, or a styryl group or its substituents, R$^6$ represents a hydrogen atom, an alkyl group, or a phenyl group or its substituents, and alternatively R$^5$ and R$^6$ optionally form a ring with carbon atoms bonded therewith; Z represents a ring hydrocarbon group or its substituents, or a heterocyclic group or its substituents; P represents an integer of 1 or 2; and q represents an integer of 1 or 2.

(9)

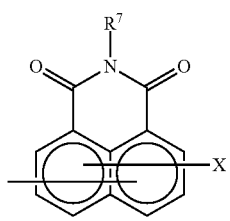

wherein R$^7$ represents a substituted or an unsubstituted hydrocarbon group; and X is same as the above-mentioned.

(10)

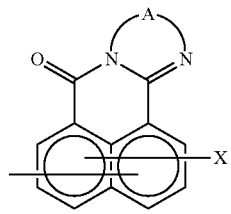

wherein A represents an of aromatic hydrocarbon bivalent group or a heterocyclic bivalent group including a nitrogen atom in the ring optionally substituted or unsubstituted; and X is same as the above-mentioned.

(11)

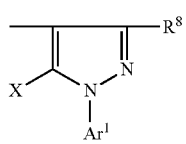

wherein R$^8$ represents an alkyl group, a carbamoyl group, a carboxy group or its esters; Ar$^1$ represents a ring hydrocarbon group or its substituents; and X is same as the above-mentioned.

(12)

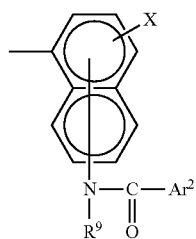

(13)

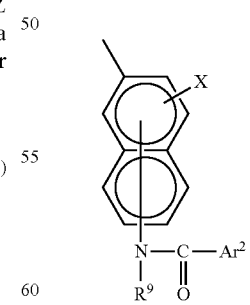

wherein R$^9$ represents a hydrogen atom, or a substituted or an unsubstituted hydrocarbon group; and Ar$^2$ a ring hydrocarbon group or its substituents.

The B in the formula (II) preferably has any one of the following formulae (III) to (X):

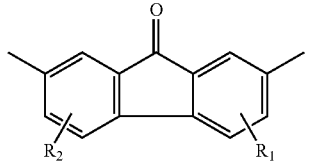 (III)

wherein $R_1$ and $R_2$ independently represent a hydrogen atom, a halogen atom, a substituted or an unsubstituted alkyl group, a substituted or an unsubstituted alkoxy group, and a carboxyl group and its esters;

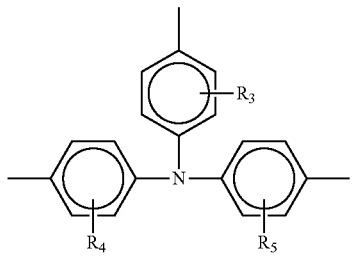 (IV)

wherein $R_3$, $R_4$ and $R_5$ independently represent a hydrogen atom, a halogen atom, a substituted or an unsubstituted alkyl group, a substituted or an unsubstituted alkoxy group, and a carboxyl group and its esters;

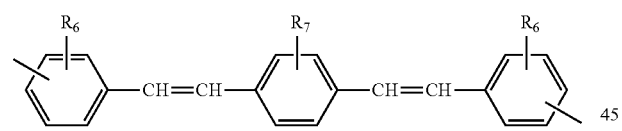 (V)

wherein $R_6$, $R_7$ and $R_8$ independently represent a hydrogen atom, a halogen atom, a substituted or an unsubstituted alkyl group, a substituted or an unsubstituted alkoxy group, and a carboxyl group and its esters;

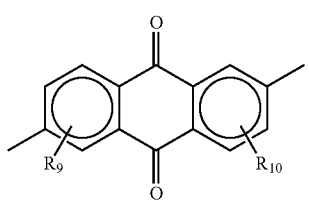 (VI)

wherein $R_9$ and $R_{10}$ independently represent a hydrogen atom, a halogen atom, a substituted or an unsubstituted alkyl group, a substituted or an unsubstituted alkoxy group, and a carboxyl group and its esters;

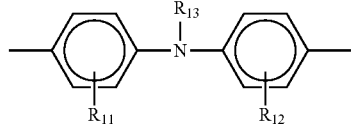 (VII)

wherein $R_{11}$, $R_{12}$ and $R_{13}$ independently represent a hydrogen atom, a halogen atom, a substituted or an unsubstituted alkyl group, a substituted or an unsubstituted alkoxy group, and a carboxyl group and its esters;

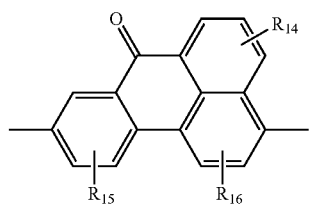 (VIII)

wherein $R_{14}$, $R_{15}$ and $R_{16}$ independently represent a hydrogen atom, a halogen atom, a substituted or an unsubstituted alkyl group, a substituted or an unsubstituted alkoxy group, and a carboxyl group and its esters;

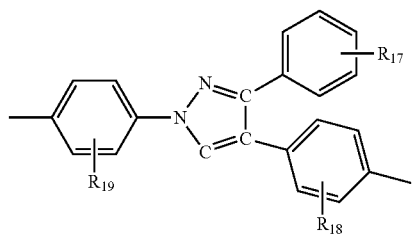 (IX)

wherein $R_{17}$, $R_{18}$ and $R_{19}$ independently represent a hydrogen atom, a halogen atom, a substituted or an unsubstituted alkyl group, a substituted or an unsubstituted alkoxy group, and a carboxyl group and its esters; and

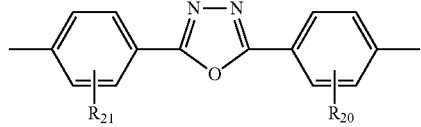 (X)

wherein $R_{21}$ and $R_{22}$ independently represent a hydrogen atom, a halogen atom, a substituted or an unsubstituted alkyl group, a substituted or an unsubstituted alkoxy group, and a carboxyl group and its esters.

Specific examples of the azo compounds having the formula (III) include compounds having the following formulae (III)-1 to (III)-14:

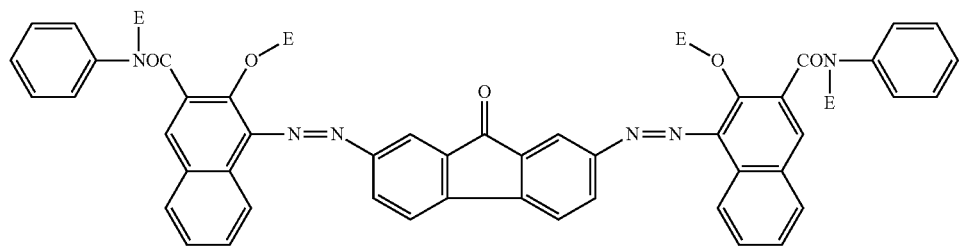
(III-1)
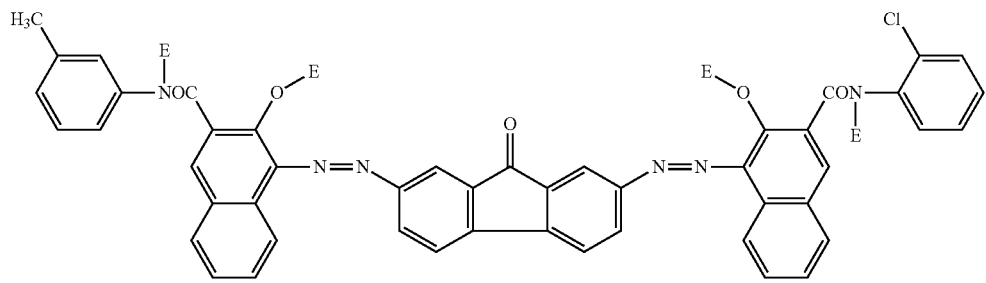
(III-2)
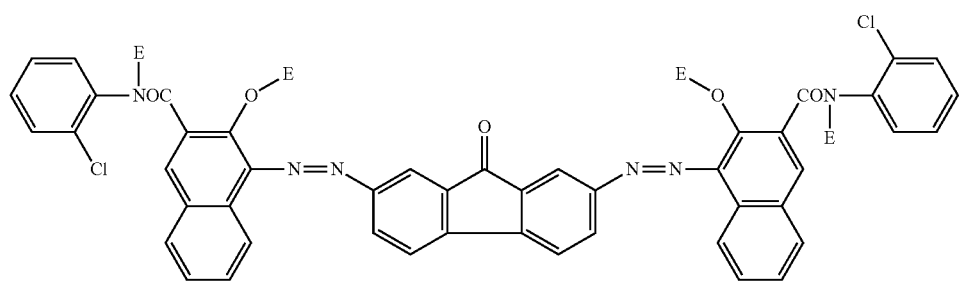
(III-3)
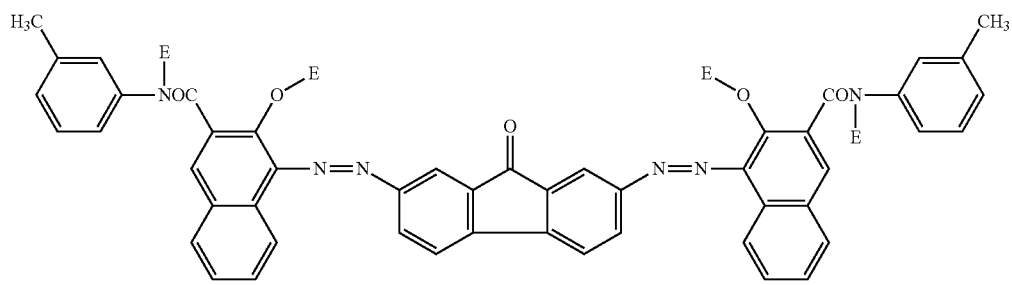
(III-4)
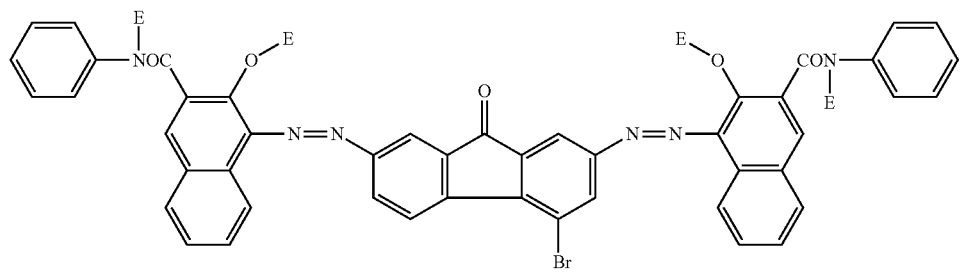
(III-5)

-continued
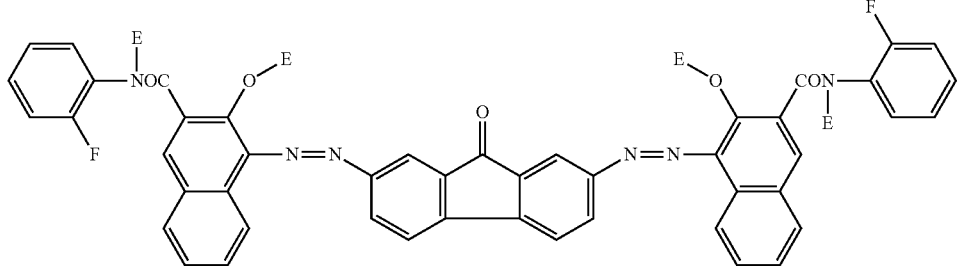
(III-6)
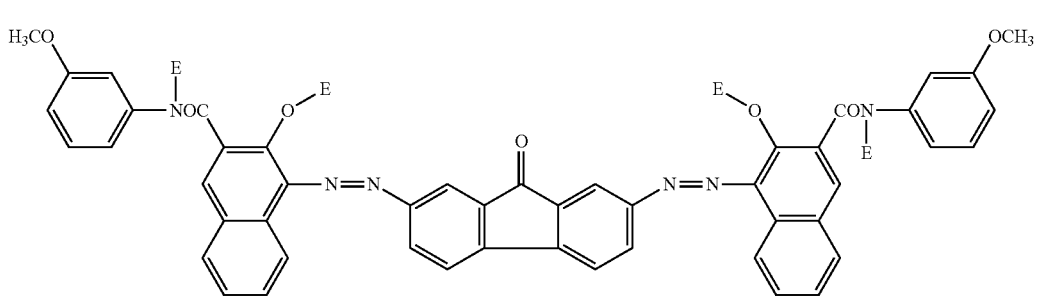
(III-7)
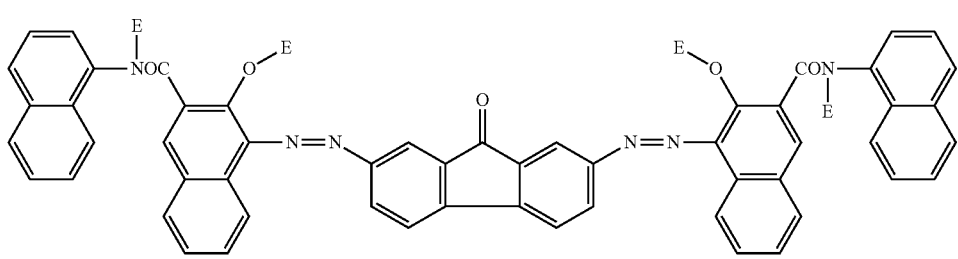
(III-8)
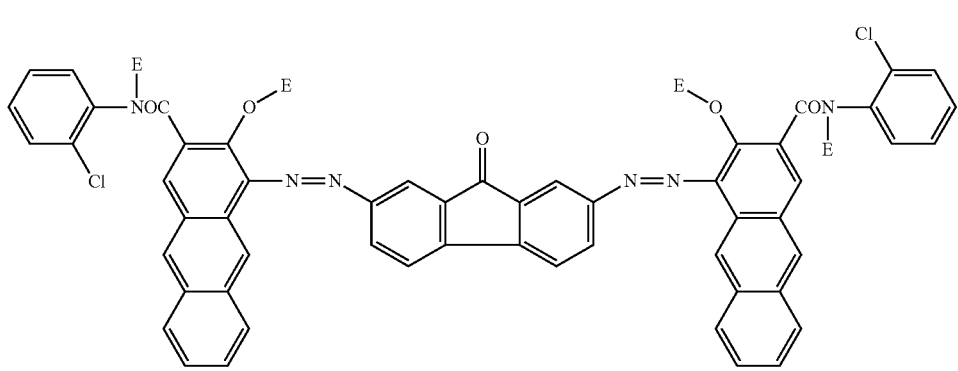
(III-9)
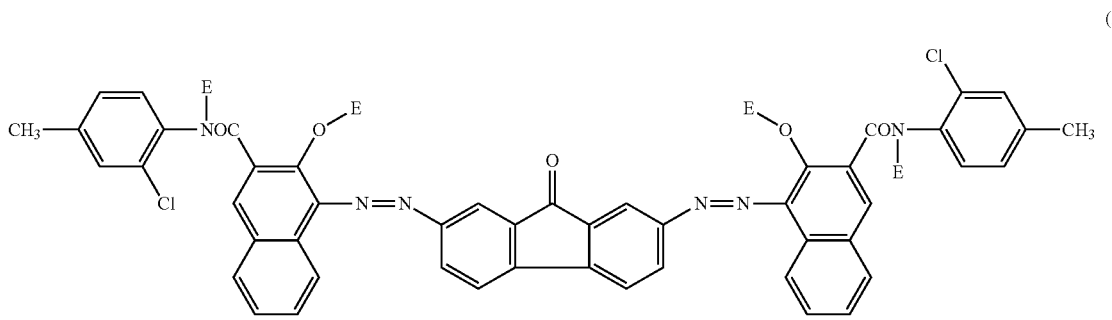
(III-10)

-continued
(III-11)
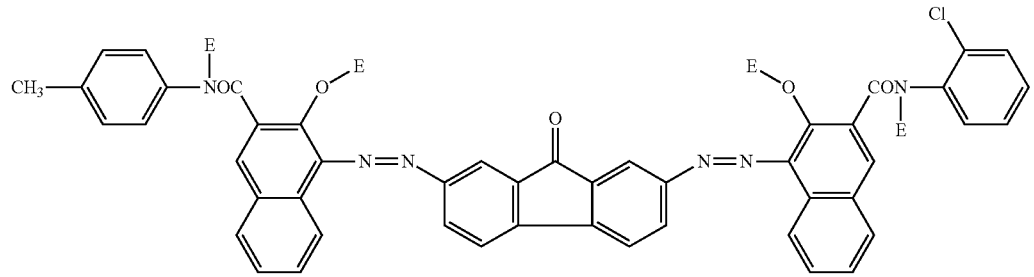
(III-12)
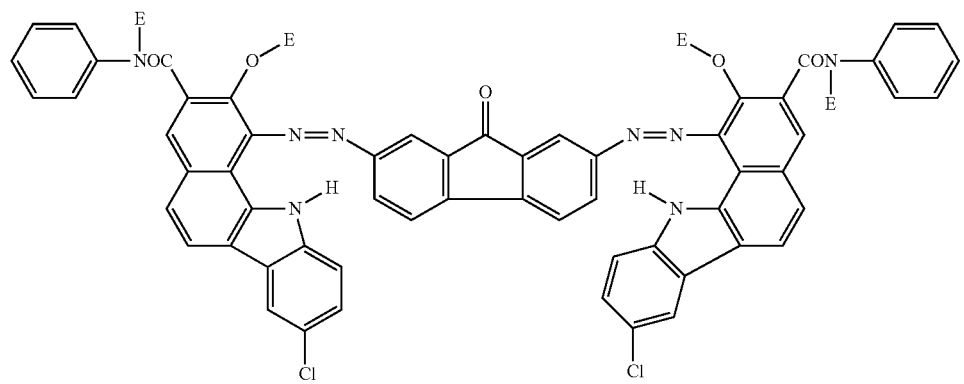
(III-13)
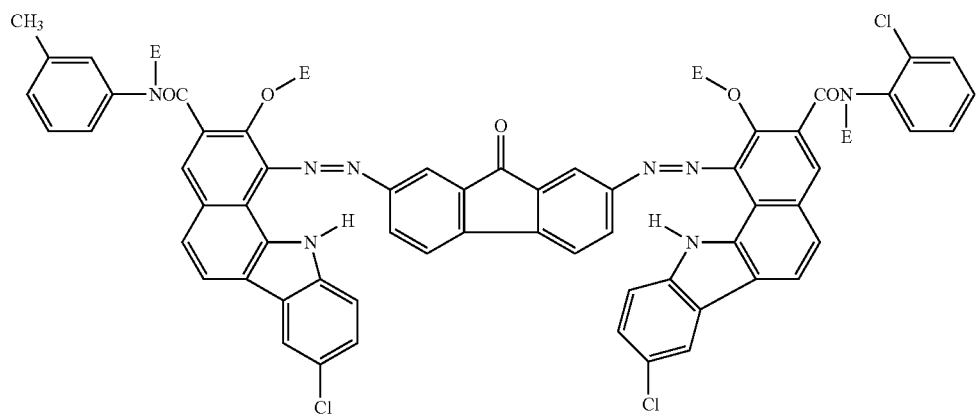
(III-14)
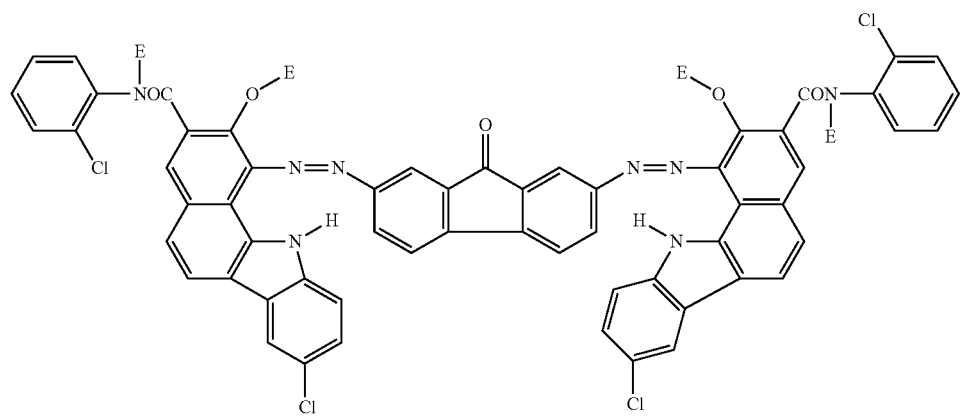

Specific examples of the azo compounds having the formula (IV) include compounds having the following formulae (IV)-1 to (IV)-5:
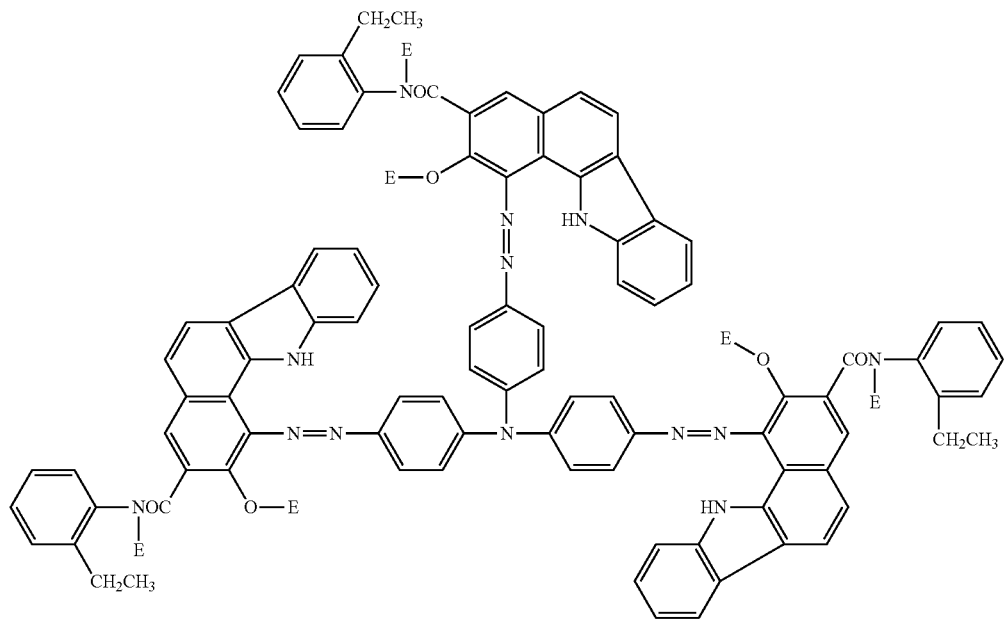
(IV-1)
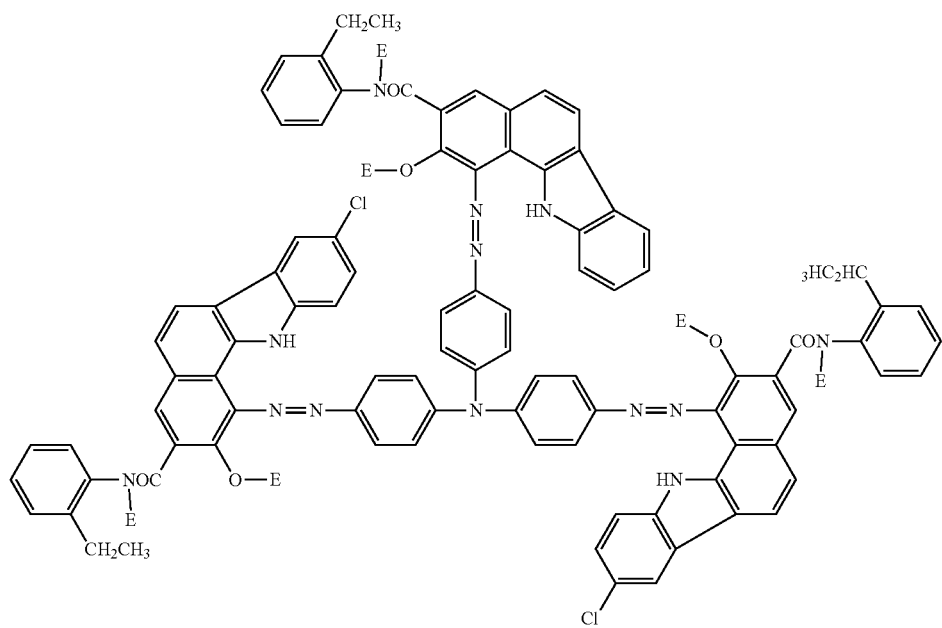
(IV-2)

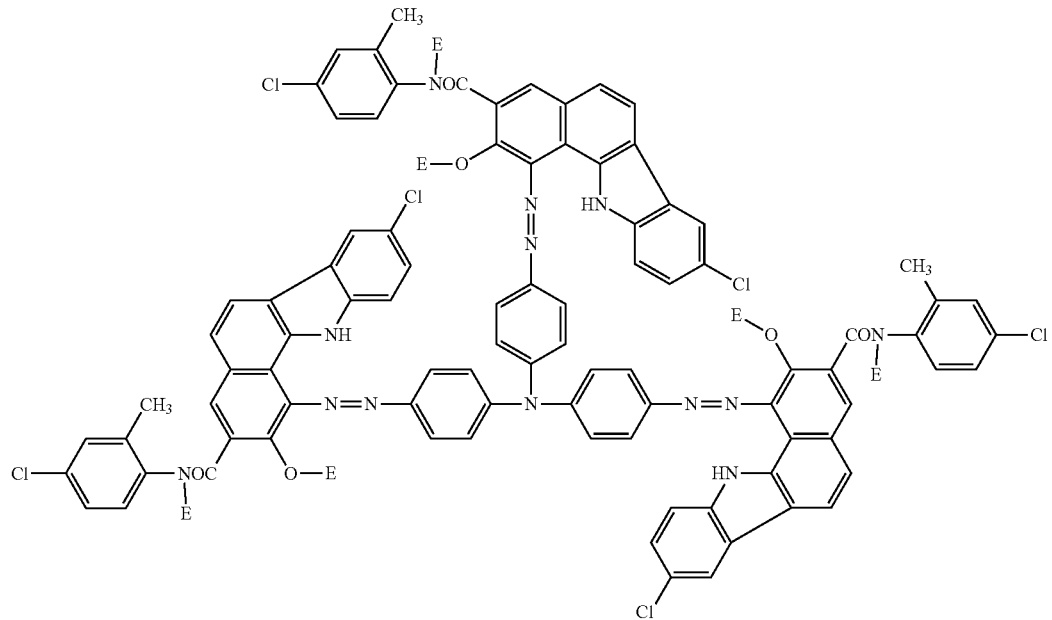
(IV-3)
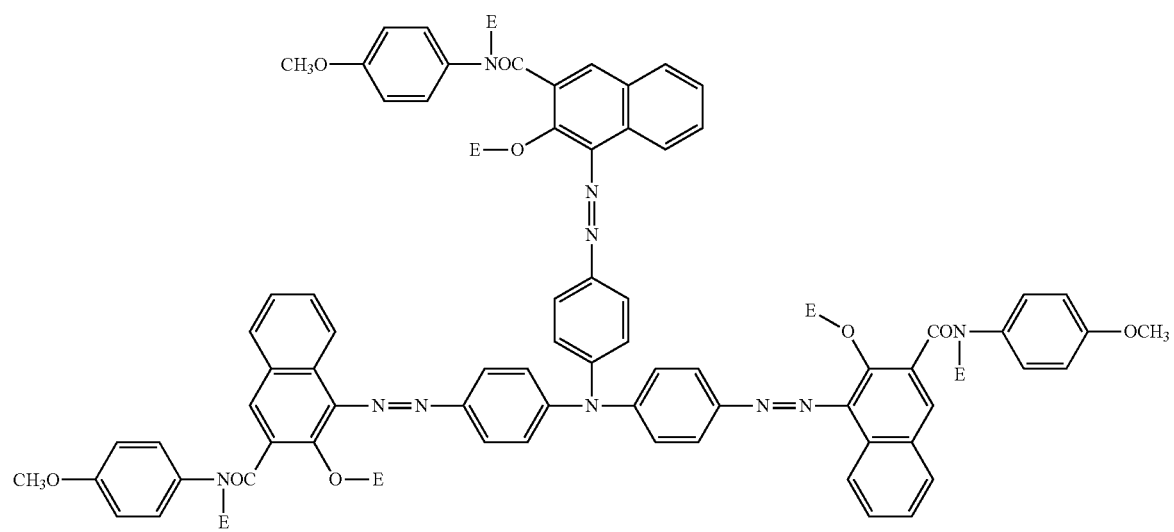
(IV-4)

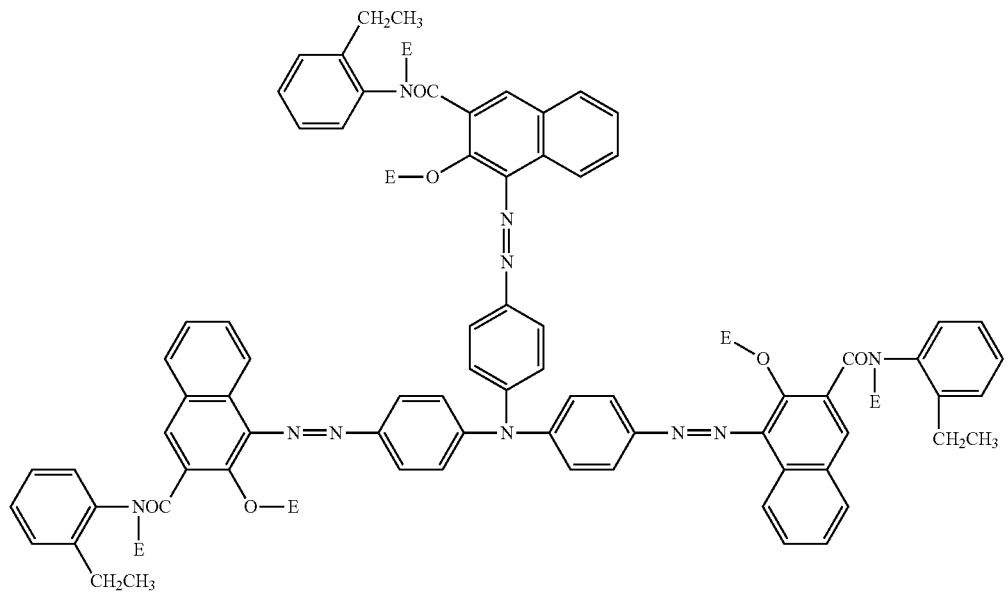
(IV-5)
Specific examples of the azo compounds having the formula (V) include compounds having the following formulae (V)-1 to (V)-7:
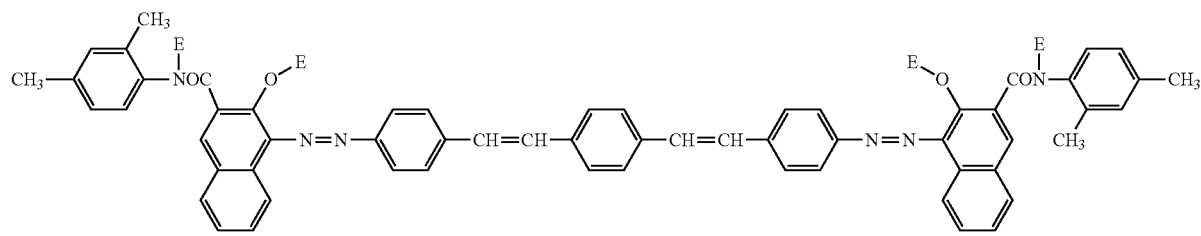
(V-1)
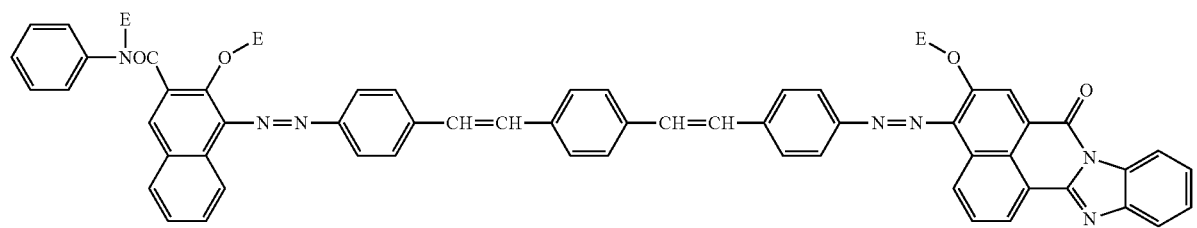
(V-2)

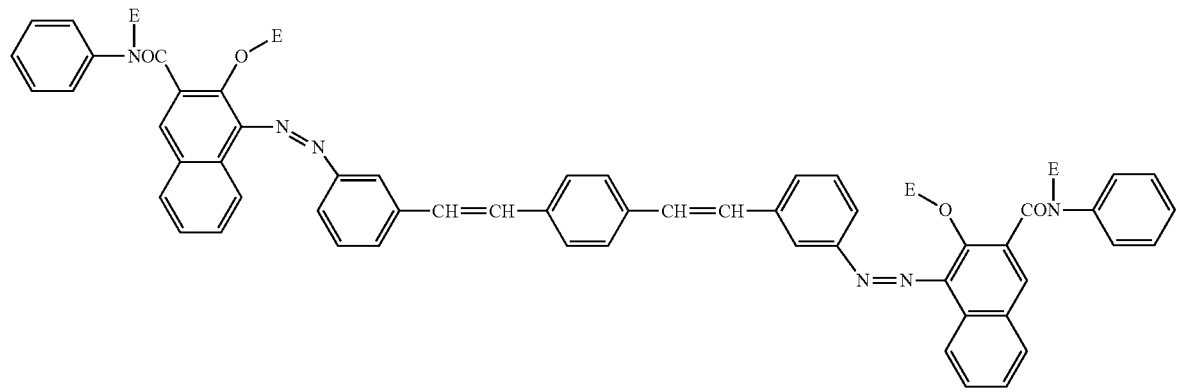
(V-3)
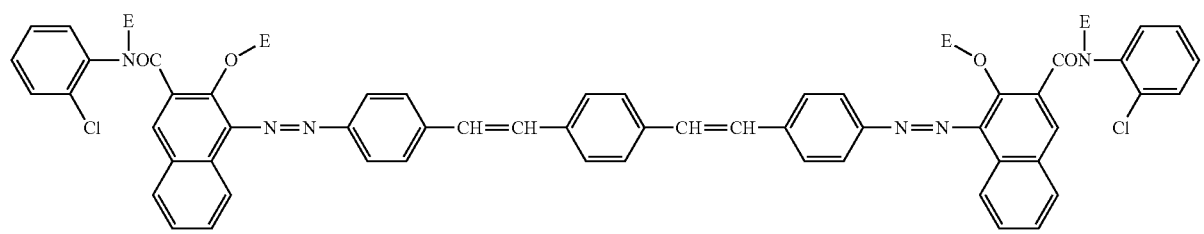
(V-4)
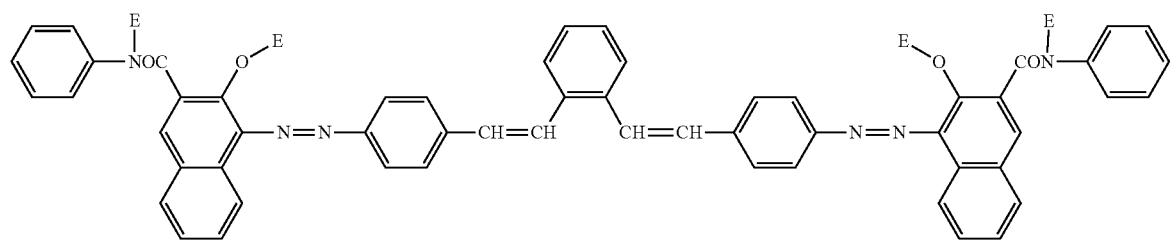
(V-5)
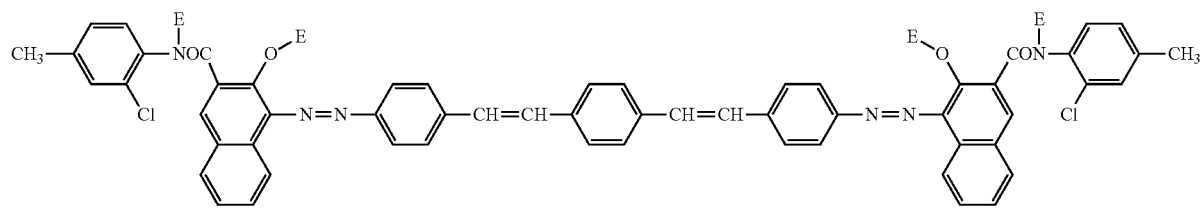
(V-6)
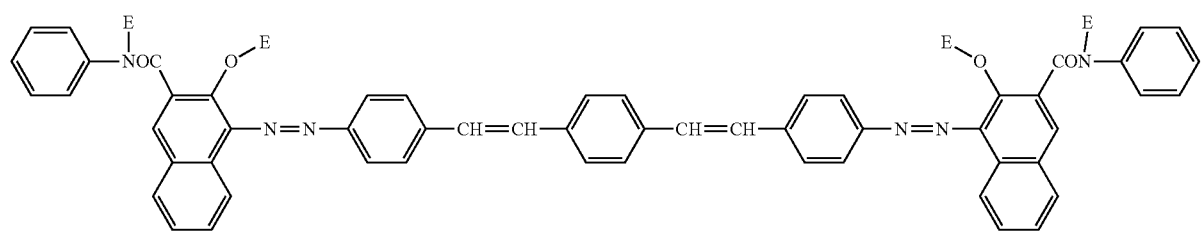
(V-7)
Specific examples of the azo compounds having the formula (VI) include compounds having the following formulae (VI)-1 to (VI)-5:

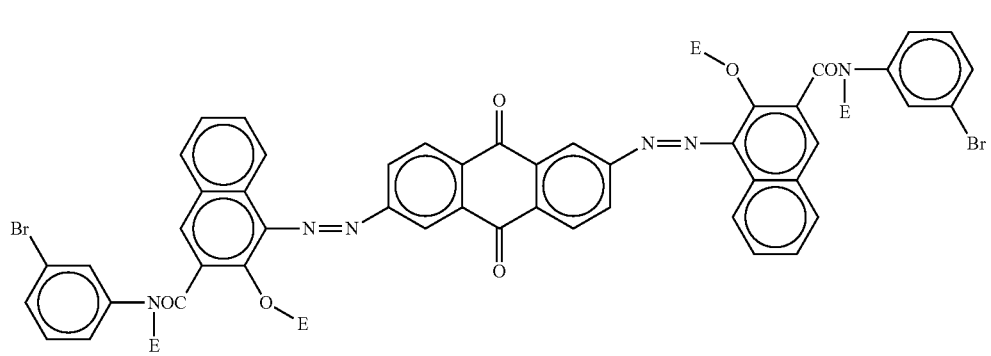
(VI-1)
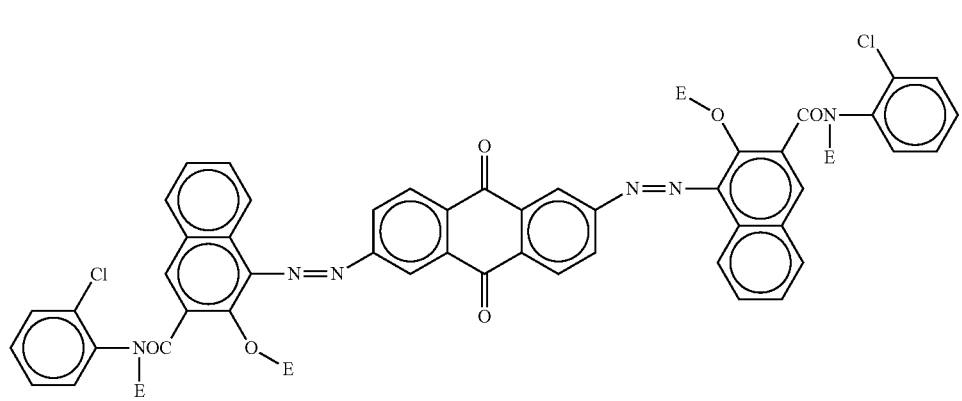
(VI-2)
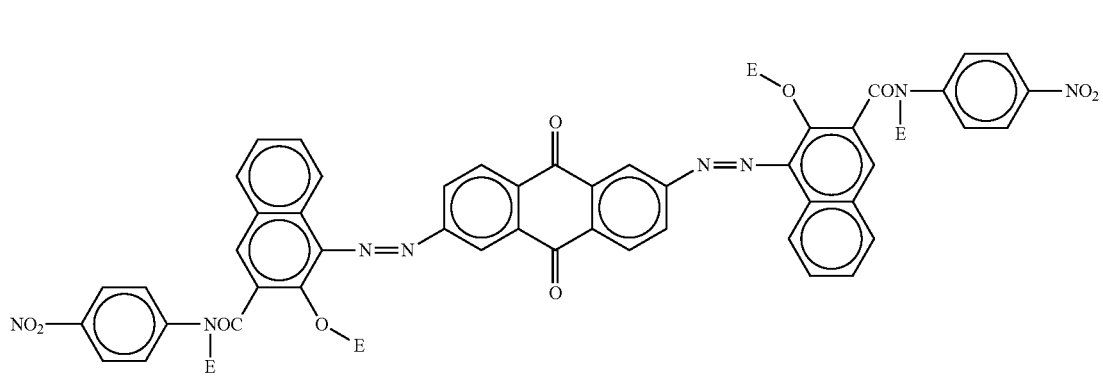
(VI-3)
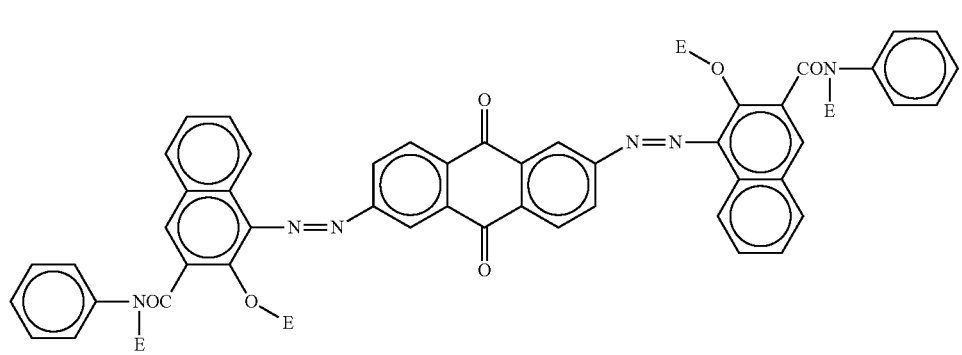
(VI-4)

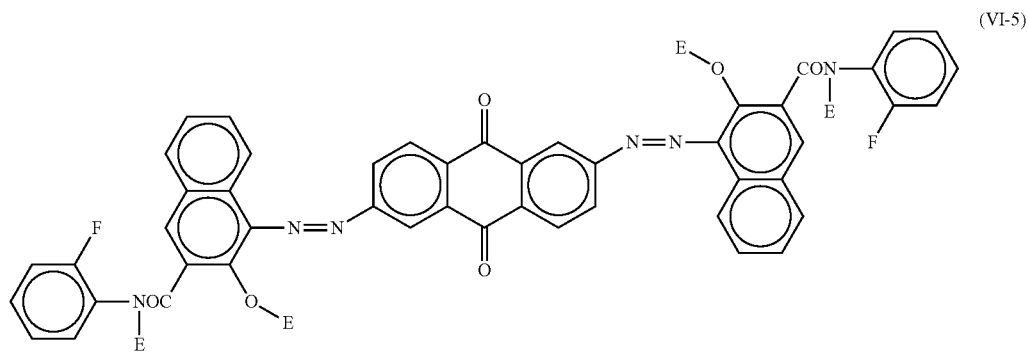
(VI-5)
Specific examples of the azo compounds having the formula (VII) include compounds having the following formulae (VII)-1 to (VII)-7:
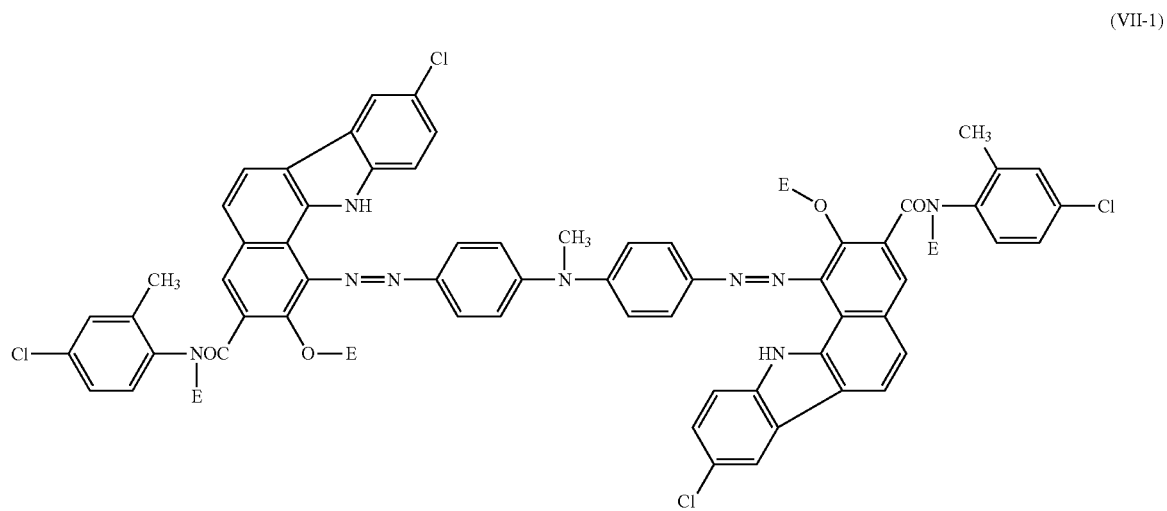
(VII-1)
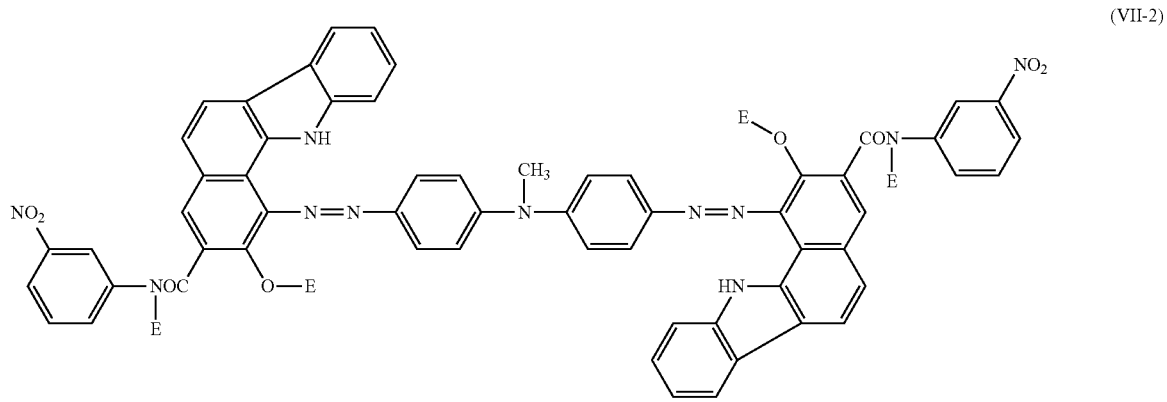
(VII-2)

-continued
(VII-3)
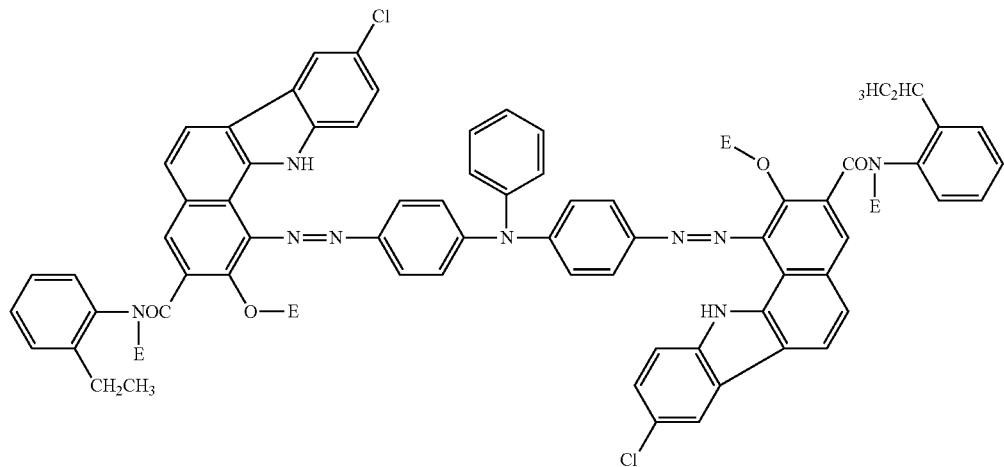
(VII-4)
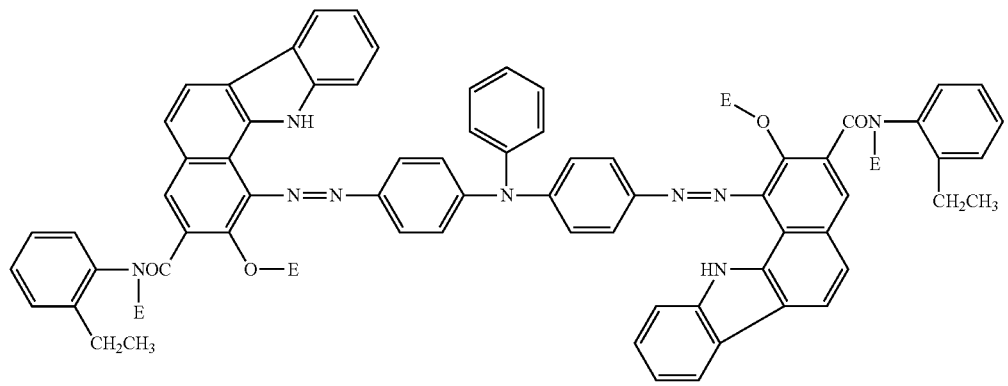
(VII-5)
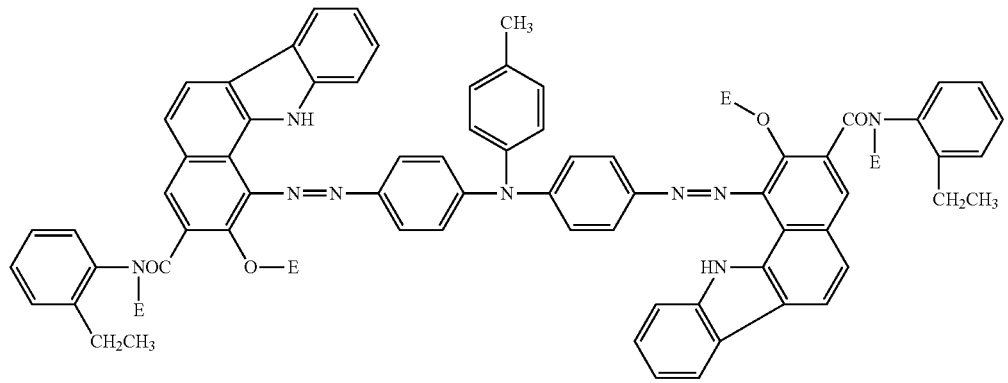
(VII-6)
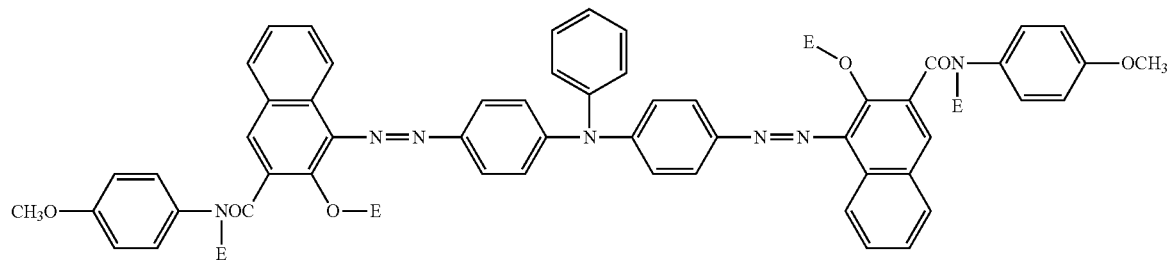

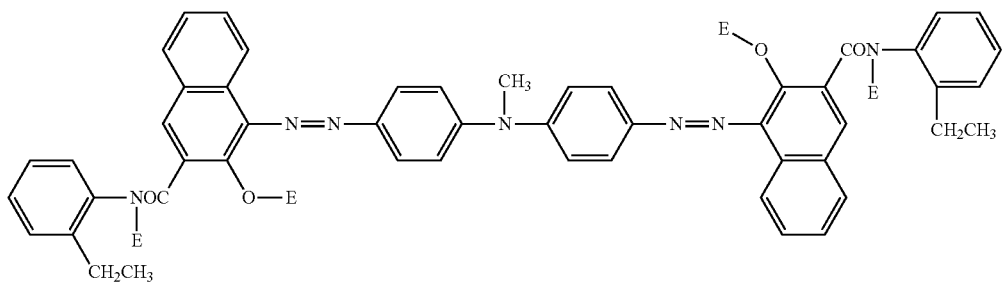
(VII-7)
Specific examples of the azo compounds having the formula (VIII) include compounds having the following formulae (VIII)-1 to (VIII)-5:
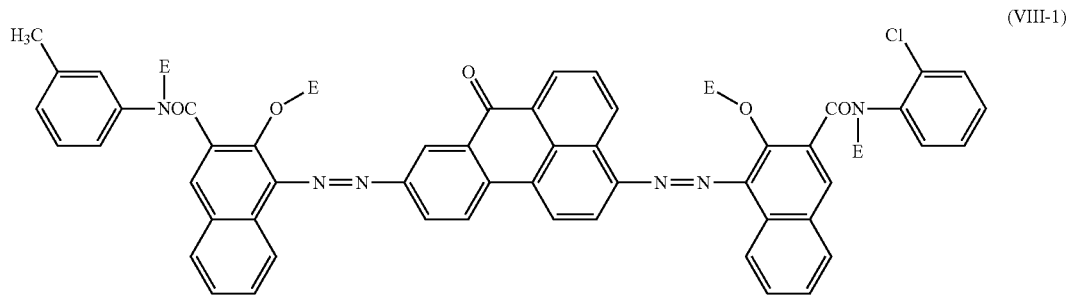
(VIII-1)
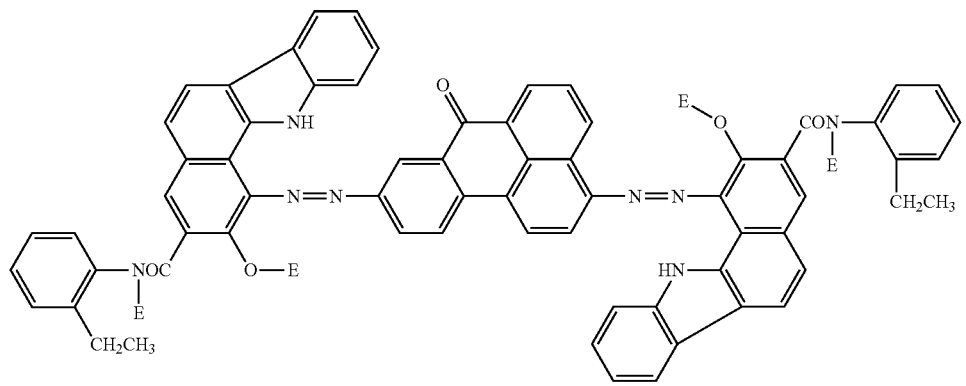
(VIII-2)
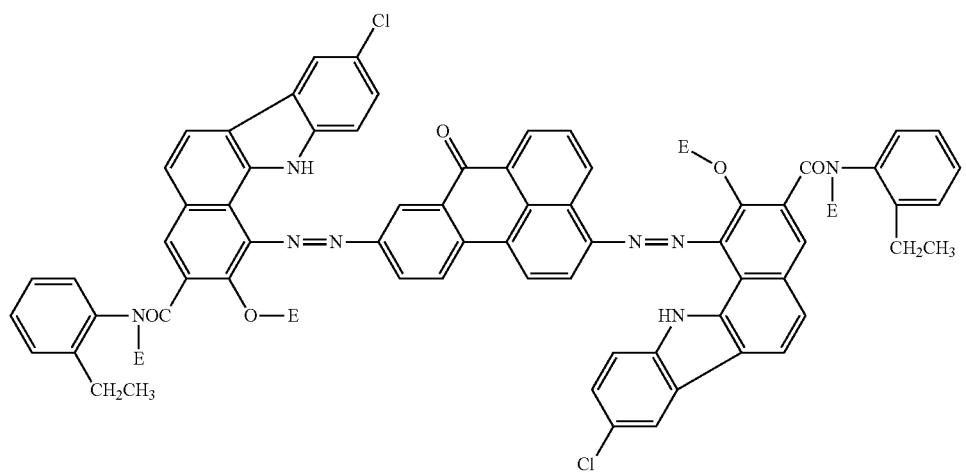
(VIII-3)

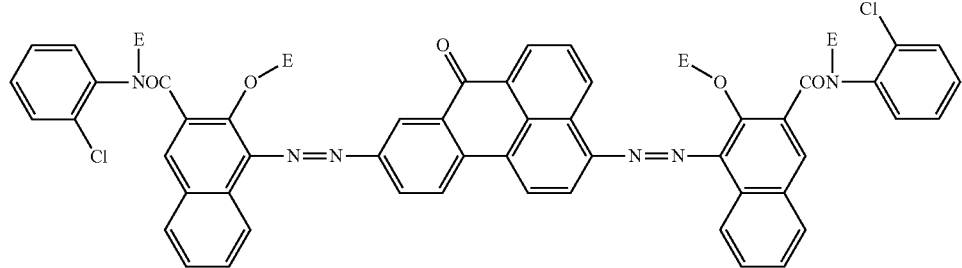
(VIII-4)
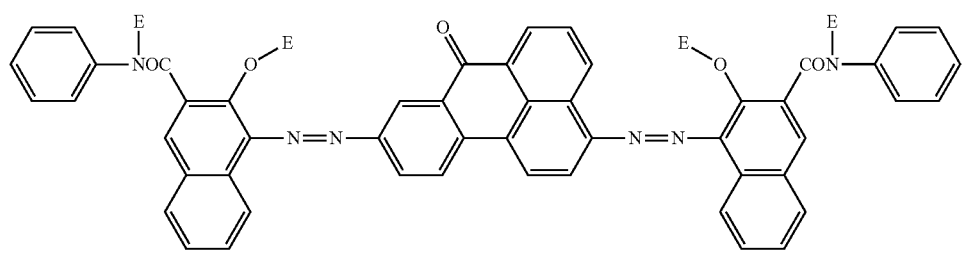
(VIII-5)
Specific examples of the azo compounds having the formula (IX) include compounds having the following formulae (IX)-1 to (IX)-4:
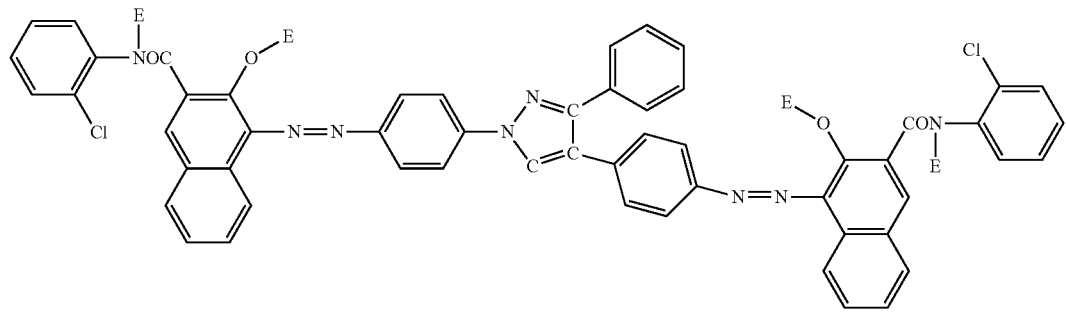
(IX-1)
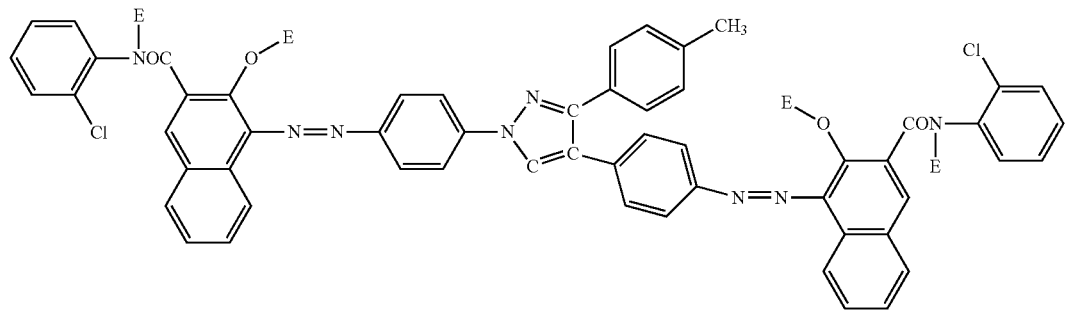
(IX-2)

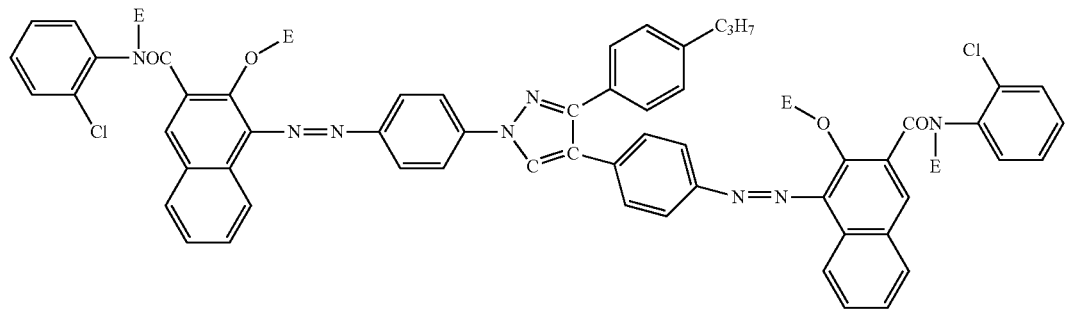
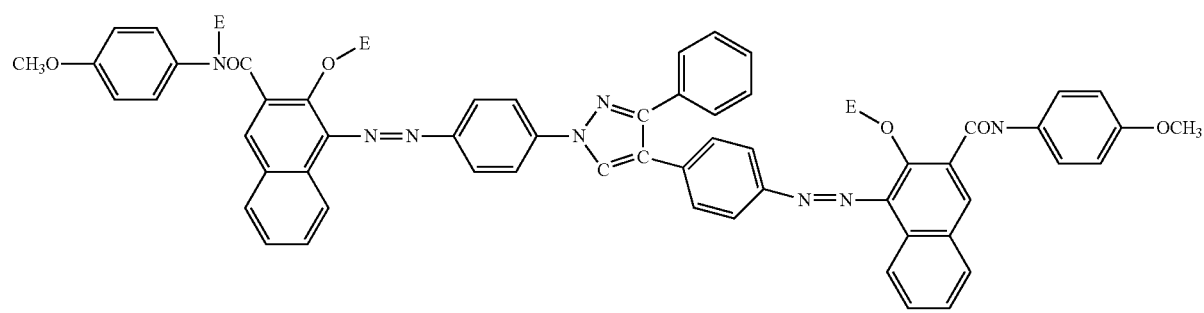
Specific examples of the azo compounds having the formula (X) include compounds having the following formulae (X)-1 to (X)-6:
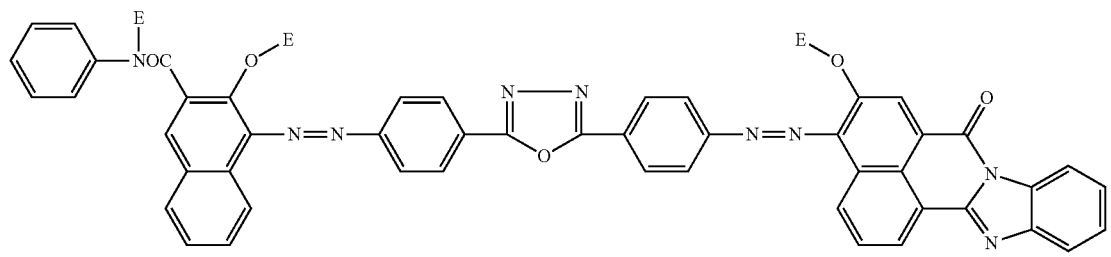
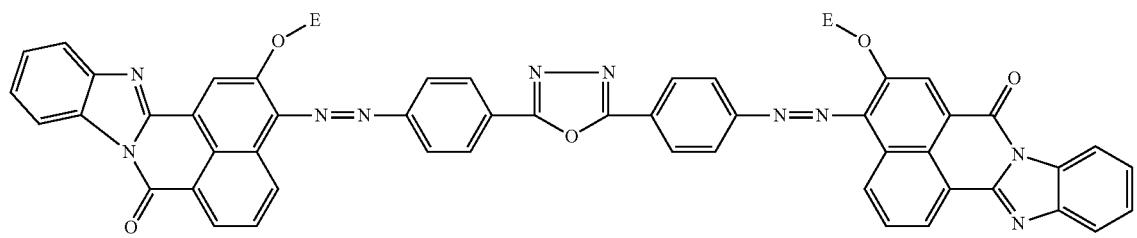
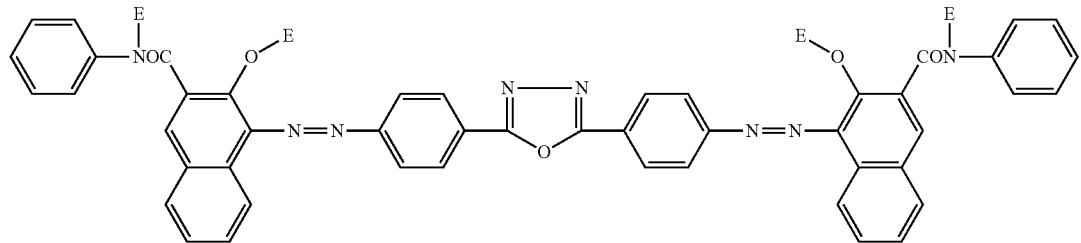

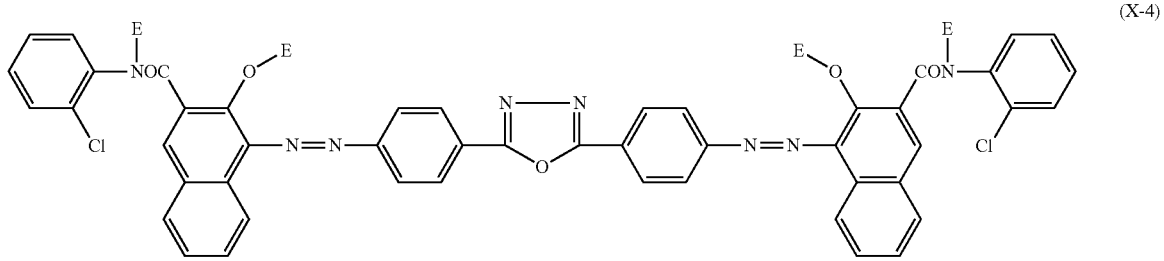

(X-4)

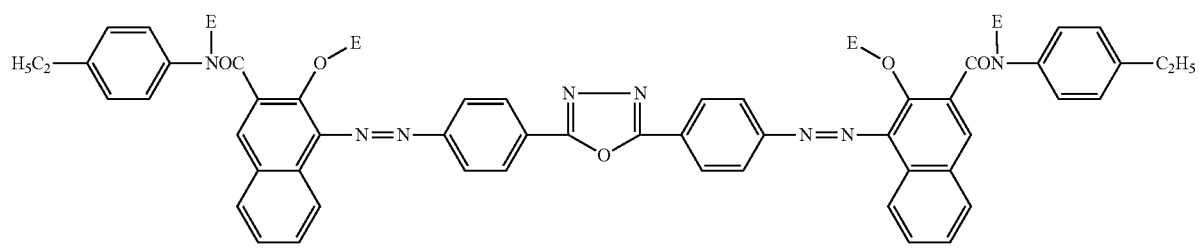

(X-5)

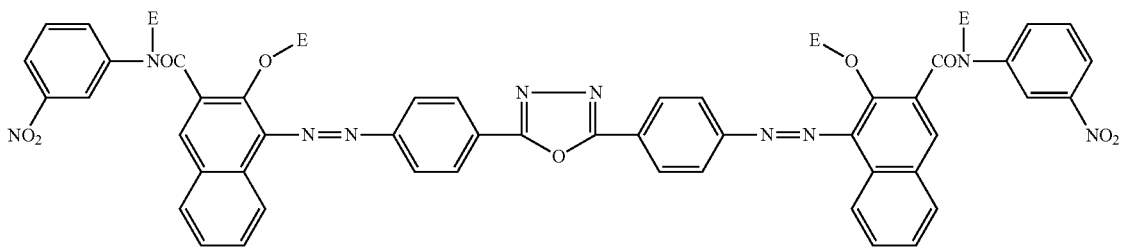

(X-6)

The compound having the formula (I) can be synthesized as disclosed in European Patents Nos. 648,770 and 648,817, or International Publication No. WO98/32802, e.g., the compound having the formula (II) and a compound having the following formula are reacted each other at a proper molar ratio in an aprotic organic solvent at from 0 to 150° C., preferably from 10 to 100° C. for 30 min to 20 hrs under the presence of a base as a catalyst.

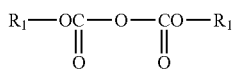

wherein $R_1$ represents a hydrogen atom, a substituted or an unsubstituted alkyl group having 4 to 10 carbon atoms, alkenyl group, alkynyl group, cycloalkyl group, cycloalkenyl group or aralkyl group.

The molar ratio depends on the number of E. Diester pyrocarbonate is preferably used a little bit more.

Specific examples of the aprotic organic solvent include ether solvents such as tetrahydrofuran and dioxane; glycol ether solvents such as ethyleneglycolmethylether and ethyleneglycolethylether; acetonitrile; N,N-dimethylformamide; N,N-dimethylacetoamide; ethylcellosolve; ethylacetate; methylacetate; dichloromethane; dichloroethane; monochlorobenzene; toluene; xylene; nitrobenzene; pyridine; picoline; quinoline; etc. Among these solvents, pyridine, tetrahydrofuran, N,N-dimethylformamide and N,N-dimethylacetoamide are preferably used.

Specific examples of the base as a catalyst include alkali metals such as sodium, kalium, and their hydroxides and carbonates; alkali metal amides such as sodium amide and kalium amide; and hydrogenated alkali metals such as hydrogenated lithium; organic aliphatic, aromatic or heterocyclic N-bases such as diazabicyclooctene, diazabicycloundecene, 4-dimethylaminopyridine, dimethylpyridine, pyridine and triethylamine. Among these bases, organic N-bases such as 4-dimethylaminopyridine, dimethylpyridine and pyridine are preferably used.

Diester pyrocarbonate having the following formula can be prepared by known methods, and commercially available.

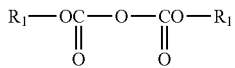

$R_1$ represents a hydrogen atom, a substituted or an unsubstituted alkyl group having 4 to 10 carbon atoms, an alkenyl group, an alkynyl group, a cycloalkyl group, a cycloalkenyl group or an aralkyl group as mentioned above, and preferably a branched alkyl group in terms of its outstandingly improved solubility.

A product having the following formula (I) can be isolated after reacted by conventional methods:

$$A(E)n \qquad (I)$$

wherein A represents a residue of an azo compound, bonded with n pieces of E group through one or more heteroatom being N or O and forming a part of the residue A; E independently represents a hydrogen atom or —C(=O)—O—R1 wherein R1 represents a substituted or unsubstituted alkyl group having 4 to 10 carbon atoms, an alkenyl group, an alkynyl group, a cycloalkyl group, a cycloalkenyl group or an aralkyl group; and n represents an integer of from 1 to 10. Particularly, the azo compound of the present invention is easy to purify by recrystallization or column chromatogram for further improving a purity thereof.

An azo pigment preparation method of converting the azo compound of the present invention having the formula (I) into an azo compound A(H)n by chemically, thermally or photolytically de-carbo esterifying the azo compound having the formula (I) will be explained.

The chemical methods prepare an azo pigment with a catalyst such as an acid or a base. Acids such as an acetic acid, a trifluoroacetic acid, a propionic acid, an acrylic acid, a benzoic acid, a hydrochloric acid, a sulfuric acid, a boric acid, a p-toluenesulfonic acid and a salicylic acid are preferably used.

The thermal methods prepare an azo pigment by heating the azo compound having the formula (I) to have a temperature of from 50 to 300° C. under the presence of no or a solvent, and preferably from 70 to 250° C. under an atmospheric pressure for 20 hrs.

The photolytic methods can use light such as a high-pressure or a low-pressure mercury lamp, a tungsten lamp, a LED lamp and a laser light source, provided the azo compound having the formula (I) absorbs the light.

Specific examples of the organic solvent include ether solvents such as tetrahydrofuran and dioxane; glycol ether solvents such as ethyleneglycolmethylether and ethyleneglycolethylether; butanol; N,N-dimethylformamide; N,N-dimethylacetoamide; ethylcellosolve; ethylacetate; butylacetate; monochlorobenzene; dichlorobenzene; toluene; xylene; anisole; cyclohexanone; nitrobenzene; pyridine; picoline; quinoline; etc.

A combination of the chemical methods, thermal methods or the photolytic methods can more efficiently prepare an azo pigment. Particularly, a combination of the chemical methods and thermal methods can prepare a high-purity azo pigment at a high yield.

An azo pigment preparation method of dissolving the azo compound having the formula (I) in an organic solvent to prepare a solution; subjecting the solution to an absorption treatment with a silica gel, alumina, florisil, an active carbon, an active earth, a diatom earth or perlite; and chemically, thermally or photolytically converting the azo compound having the formula (I) into an azo compound A(H)n will be explained.

Specific examples of the organic solvent include ether solvents such as tetrahydrofuran and dioxane; glycol ether solvents such as ethyleneglycolmethylether and ethyleneglycolethylether; butanol; N,N-dimethylformamide; N,N-dimethylacetoamide; ethylcellosolve; ethylacetate; butylacetate; dichloromethane; chloroform; carbon tetrachloride; dichloroethane; monochlorobenzene; dichlorobenzene; toluene; xylene; anisole; n-hexane; cyclohexanone; nitrobenzene; pyridine; picoline; quinoline; and their combinations.

The absorption treatment includes column chromatography and filtration with an absorbent at room temperature or when heated. In addition, a combination of the absorption treatment and a recrystallization can more efficiently prepare a high-purity azo pigment.

The azo compound of the present invention is used for organic photoconductive materials, particularly as a charge generation material for various electrophotographic photoreceptors, e.g., (1) a single-layered photoreceptor formed of an electroconductive substrate and a photoconductive layer including the azo compound, a binder resin and an optional sensitizer as main components on the electroconductive substrate; (2) the single-layered photoreceptor of (1), the photoconductive layer of which further includes a charge transport material; (3) a multilayered photoreceptor formed of an electroconductive substrate, a charge generation layer including the azo compound as a main component on the electroconductive substrate, and further a charge transport layer including a charge transport material and a binder resin as main components on the charge generation layer; and (4) the multilayered photoreceptor of (3), the charge generation layer and the charge transport layer of which are reversely layered.

In addition, the azo compound of the present invention can also be used for other color materials such as those for recording media and color filters because of having good solubility in an organic solvent.

Having generally described this invention, further understanding can be obtained by reference to certain specific examples which are provided herein for the purpose of illustration only and are not intended to be limiting. In the descriptions in the following examples, the numbers represent weight ratios in parts, unless otherwise specified.

EXAMPLES

Example 1

Preparation of Compound III-3

0.83 g of a precursor of the compound III-3 (E=H) and 2.6 g (12 times mol) of pyrocarboxylic acid di-tert-butyl ester were dispersed in 150 ml of dehydrated pyridine, and after the dispersion was stirred at room temperature for 15 min, the dispersion was heated to have a temperature about 50° C. and reacted for 30 min. The dispersion gradually became reddish and a uniform solution was prepared. The solution was cooled to have a room temperature and the solvent was distilled off under reduced pressure. Then, about 50 ml of ethylacetate were added thereto to prepare 1.18 g of a red powder (yield rate: 95.3%). The red powder was further purified by column chromatogram (silica gel/chloroform).

Elemental Analysis ($C_{67}H_{60}N_6O_{13}Cl_2$) (All E:$C_5H_9O_2$)

|  | C | H | N |
|---|---|---|---|
| Found. (%) | 65.53 | 4.98 | 7.04 |
| Calcd. (%) | 65.52 | 4.92 | 6.84 |

An absorption by saturated hydrocarbon was observed at 2,980 $cm^{-1}$ and an absorption based on a stretching vibration of carbonate C=O was observed at 1,760 $cm^{-1}$ in an infrared absorption spectrum (KBr tablet method) of the powder.

Example 2

Preparation of Compound III-4

0.79 g of a precursor of the compound III-4 (E=H) and 2.6 g (12 times mol) of pyrocarboxylic acid di-tert-butyl ester were dispersed in 150 ml of dehydrated pyridine, and after the dispersion was stirred at room temperature for 15 min, the dispersion was heated to have a temperature about 50° C. and reacted for 30 min. The dispersion gradually became reddish and a uniform solution was prepared. The solution was cooled to have a room temperature and the solvent was distilled off under reduced pressure. Then, about 50 ml of ethylacetate were added thereto to prepare 1.02 g of a red powder (yield rate: 85.6%).

Elemental Analysis ($C_{69}H_{66}N_6O_{13}$) (All E:$C_5H_9O_2$)

|  | C | H | N |
|---|---|---|---|
| Found. (%) | 69.69 | 5.55 | 7.05 |
| Calcd. (%) | 69.80 | 5.60 | 7.08 |

An absorption by saturated hydrocarbon was observed at 2,980 $cm^{-1}$ and an absorption based on a stretching vibration of carbonate C=O was observed at 1,760 $cm^{-1}$ in an infrared absorption spectrum (KBr tablet method) of the powder.

Example 3

Preparation of Compound III-2

1.61 g of a precursor of the compound III-2 (E=H) and 4.3 g (12 times mol) of pyrocarboxylic acid di-tert-butyl ester were dispersed in 50 ml of dehydrated pyridine and 200 ml of dehydrated N,N-dimethylformamide, and after the dispersion was stirred at room temperature for 15 min, the dispersion was heated to have a temperature about 50° C. and reacted for 2 hrs. The dispersion gradually became reddish and a uniform solution was prepared. The solution was cooled to have a room temperature and about 100 ml of ethylacetate were added thereto to prepare 2.24 g of a red powder (yield rate: 93%).

Elemental Analysis ($C_{58}H_{47}N_6O_9Cl$) (All E:$C_5H_9O_2$)

|  | C | H | N |
|---|---|---|---|
| Found. (%) | 67.18 | 5.09 | 6.84 |
| Calcd. (%) | 67.63 | 5.26 | 6.96 |

An absorption by saturated hydrocarbon was observed at 2,980 $cm^{-1}$ and an absorption based on a stretching vibration of carbonate C=O was observed at 1,765 $cm^{-1}$ in an infrared absorption spectrum (KBr tablet method) of the powder.

Example 4

Preparation of Compound III-3

0.21 g of a precursor of the compound III-3 (E=H) and 0.43 g (6 times mol) of pyrocarboxylic acid di-benzyl ester and 0.54 g of 3,4-dimethylpyridine were dispersed in 50 ml of dehydrated N,N-dimethylformamide, and after the dispersion was stirred at room temperature for 15 min, the dispersion was heated to have a temperature of 100° C. and reacted for 6 hrs. The dispersion gradually became reddish and a uniform solution was prepared. The solution was cooled to have a room temperature and the solvent was distilled off under reduced pressure. Then, about 50 ml of toluene were added thereto to prepare 0.28 g of a red powder (yield rate: 92.0%).

An absorption by saturated hydrocarbon was observed at 2,980 $cm^{-1}$ and an absorption based on a stretching vibration of carbonate C=O was observed at 1,760 $cm^{-1}$ in an infrared absorption spectrum (KBr tablet method) of the powder.

Example 5

Preparation of Compound IV-1

2.93 g of a precursor of the compound IV-1 (E=H) and 6.5 g (15 times mol) of pyrocarboxylic acid di-tert-butyl ester were dispersed in 250 ml of dehydrated pyridine, and after the dispersion was stirred at room temperature for 15 min, the dispersion was heated to have a temperature of 40° C. and reacted for 40 min. The dispersion gradually became reddish violet and a uniform solution was prepared. The solution was cooled to have a room temperature and the solvent was distilled off under reduced pressure. Then, about 100 ml of cyclohexane were added thereto to prepare 2.91 g of a red powder (yield rate: 71.0%).

Elemental Analysis ($C_{123}H_{117}N_{13}O_{18}Cl$) (All E:$C_5H_9O_2$)

|  | C | H | N |
|---|---|---|---|
| Found. (%) | 71.28 | 5.65 | 9.11 |
| Calcd. (%) | 71.53 | 5.71 | 8.82 |

An absorption by saturated hydrocarbon was observed at 2,980 $cm^{-1}$ and an absorption based on a stretching vibration of carbonate C=O was observed at 1,765 $cm^{-1}$ in an infrared absorption spectrum (KBr tablet method) of the powder.

Example 6

Preparation of Compound V-1

0.92 g of a precursor of the compound V-1 (E=H) and 2.6 g (12 times mol) of pyrocarboxylic acid di-tert-butyl ester were dispersed in 150 ml of dehydrated pyridine, and after the dispersion was stirred at room temperature for 15 min, the dispersion was heated to have a temperature about 50° C. and reacted for 40 min. The dispersion gradually became reddish orange and a uniform solution was prepared. The solution was cooled to have a room temperature and the solvent was distilled off under reduced pressure. Then, about 50 ml of ethylacetate were added thereto to prepare 1.16 g of a red powder (yield rate: 88.0%).

Elemental Analysis ($C_{69}H_{66}N_6O_{13}$) (All E:$C_5H_9O_2$)

|  | C | H | N |
|---|---|---|---|
| Found. (%) | 72.69 | 6.03 | 6.45 |
| Calcd. (%) | 72.93 | 6.12 | 6.38 |

An absorption by saturated hydrocarbon was observed at 2,975 $cm^{-1}$ and an absorption based on a stretching vibration of carbonate C=O was observed at 1,760 $cm^{-1}$ in an infrared absorption spectrum (KBr tablet method) of the powder.

Example 7

Preparation of Compound VI-1

0.94 g of a precursor of the compound VI-1 (E=H) and 2.6 g (12 times mol) of pyrocarboxylic acid di-tert-butyl ester were dispersed in 150 ml of dehydrated pyridine, and after the dispersion was stirred at room temperature for 15 min, the dispersion was heated to have a temperature about 50° C. and reacted for 2 hrs. The dispersion gradually became reddish and a uniform solution was prepared. The solution was cooled to have a room temperature and the solvent was distilled off under reduced pressure. Then, about 50 ml of ethylacetate were added thereto to prepare 1.11 g of a red powder (yield rate: 83.2%).

Elemental Analysis ($C_{48}H_{24}N_6O_6Br_2$) (All E:$C_5H_9O_2$)

|  | C | H | N |
|---|---|---|---|
| Found. (%) | 60.66 | 4.73 | 6.35 |
| Calcd. (%) | 60.72 | 4.50 | 6.25 |

An absorption by saturated hydrocarbon was observed at 2,980 cm$^{-1}$ and an absorption based on a stretching vibration of carbonate C═O was observed at 1,760 cm$^{-1}$ in an infrared absorption spectrum (KBr tablet method) of the powder.

Example 8

Preparation of Compound VII-2

1.20 g of a precursor of the compound VII-2 (E=H) and 1.6 g (12 times mol) of pyrocarboxylic acid di-benzyl ester were dispersed in 150 ml of dehydrated pyridine, and after the dispersion was stirred at room temperature for 15 min, the dispersion was heated to have a temperature about 50° C. and reacted for 1 hr. The dispersion gradually became reddish violet and a uniform solution was prepared. The solution was cooled to have a room temperature and the solvent was distilled off under reduced pressure. Then, about 50 ml of cyclohexane were added thereto to prepare 1.60 g of a red powder (yield rate: 79.6%).

Elemental Analysis ($C_{122}H_{83}N_9O_{16}Cl_2$) (All: E:$C_8H_7O_2$)

|  | C | H | N |
|---|---|---|---|
| Found. (%) | 72.98 | 4.30 | 6.45 |
| Calcd. (%) | 73.20 | 4.18 | 6.30 |

An absorption by saturated hydrocarbon was observed at 2,980 cm$^{-1}$ and an absorption based on a stretching vibration of carbonate C═O was observed at 1,760 cm$^{-1}$ in an infrared absorption spectrum (KBr tablet method) of the powder.

Example 9

Preparation of Compound VIII-5

0.81 g of a precursor of the compound VIII-5 (E=H) and 2.7 g (12 times mol) of pyrocarboxylic acid di-tert-butyl ester were dispersed in 150 ml of dehydrated pyridine, and after the dispersion was stirred at room temperature for 15 min, the dispersion was heated to have a temperature about 50° C. and reacted for 2 hrs. The dispersion gradually became reddish and a uniform solution was prepared. The solution was cooled to have a room temperature and the solvent was distilled off under reduced pressure. Then, about 50 ml of ethylacetate were added thereto to prepare 1.10 g of a red powder (yield rate: 86.6%).

Elemental Analysis ($C_{75}H_{72}N_6O_{13}$) (All E:$C_5H_9O_2$)

|  | C | H | N |
|---|---|---|---|
| Found. (%) | 71.20 | 5.79 | 6.35 |
| Calcd. (%) | 71.19 | 5.74 | 6.64 |

An absorption by saturated hydrocarbon was observed at 2,980 cm$^{-1}$ and an absorption based on a stretching vibration of carbonate C═O was observed at 1,760 cm$^{-1}$ in an infrared absorption spectrum (KBr tablet method) of the powder.

Example 10

Preparation of Compound X-1

0.16 g of a precursor of the compound X-1 (E=H) and 0.52 g (12 times mol) of pyrocarboxylic acid di-tert-butyl ester were dispersed in 30 ml of dehydrated pyridine, and after the dispersion was stirred at room temperature for 15 min, the dispersion was heated to have a temperature about 50° C. and reacted for 2 hrs. The dispersion gradually became reddish and a uniform solution was prepared. The solution was cooled to have a room temperature and the solvent was distilled off under reduced pressure. Then, about 50 ml of ethylacetate were added thereto to prepare 0.16 g of a red powder (yield rate: 80%).

Elemental Analysis ($C_{69}H_{66}N_6O_{13}$) (All E:$C_5H_9O_2$)

|  | C | H | N |
|---|---|---|---|
| Found. (%) | 67.85 | 4.67 | 11.11 |
| Calcd. (%) | 68.38 | 4.75 | 11.21 |

An absorption by saturated hydrocarbon was observed at 2,980 cm$^{-1}$ and an absorption based on a stretching vibration of carbonate C═O was observed at 1,760 cm$^{-1}$ in an infrared absorption spectrum (KBr tablet method) of the powder.

Application Example

Based on Japanese Published Unexamined Application No. 2007-108682

An electrophotographic photoreceptor was prepared as follows.

30 parts of a metal-free phthalocyanine pigment Fastogen Blue 8120B from Dainippon Ink And Chemicals, Inc. as a charge generation material were dispersed with 970 parts of cyclohexanone in a ball mill for 2 hrs to prepare a charge generation material dispersion. Separately, 49 parts of a polycarbonate resin (Z-polyca having a viscosity-average molecular weight of 40,000 from Teijin Chemicals Ltd.), 20 parts of the azo compound having the formula III-3, 29.5 parts of a charge transport material having the following formula (I) and 0.1 parts of a silicone oil (KF50-100CS from Shin-Etsu Chemical Co., Ltd.) were dissolved in 340 parts of tetrahydrofuran to prepare a solution.

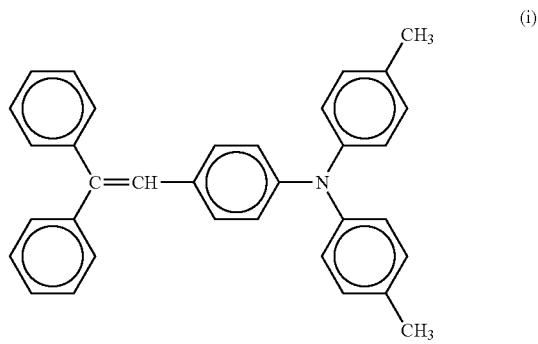

(i)

66.6 parts of the charge generation material dispersion were added to the solution and stirred therein to prepare a photosensitive layer coating liquid.

The photosensitive layer coating liquid was dip-coated on an aluminum drum having a circumferential fluctuation not greater than 20 μm, a length of 340 mm and a diameter of 30 mm. The coated drum was dried at 120° C. for 15 min to form a photosensitive layer having a thickness of 25 μm thereon.

The thus prepared electrophotographic photoreceptor was installed in a modified IPSio Color 8100 from Ricoh Company, Ltd., which is modified to have a writing LD having a wavelength of 780 nm and a positively charged-photoreceptor. Under the following conditions, 50,000 pieces of a full-color image which is a mixture of a rectangle patch having an image area of 6% and letters were produced thereby to evaluate a dark space potential, a bright space potential and image quality at the beginning of and after production of the 50,000 images. The results are shown in Table 1.

The dark space, bright space and image quality were evaluated as follows.

Dark space potential: A surface potential of the photoreceptor when moved to a developing position after primarily charged. Initially, the photoreceptor was charged at a voltage of +700 V and a constant voltage afterward.

Bright space potential: A surface potential of the photoreceptor when wholly irradiated and moved to a developing position after charged.

Image quality: whether the full-color image had background fouling when unevenly charged.

TABLE 1

|  | Dark space potential (+V) | Bright space potential (+V) | Image quality |
|---|---|---|---|
| Beginning | 700 | 90 | NIL |
| After 50,000 | 680 | 130 | NIL |

As is apparent from the above-mentioned explanation, the azo compound of the present invention is effectively used as an organic photoconductive material for use in a high-sensitive electrophotographic photoreceptor for high-speed copiers.

Example 11

0.49 g of the azo compound (III-3) (E=$C_5H_9O_2$) prepared in Example 1 and 1.0 g of trifluoroacetic acid were reacted with 50 ml of o-xylene for 8 hrs under a reflux temperature. The reactant gradually became blackish and a navy-blue material precipitated. At room temperature, the precipitate was filtered with a fluoro pore having a size of 0.1 micron and washed with 50 ml of tetrahydrofuran to prepare a raisin powder.

The absorption by saturated hydrocarbon observed at 2,980 $cm^{-1}$ and the absorption based on a stretching vibration of carbonate C=O observed at 1,760 $cm^{-1}$ in an infrared absorption spectrum (KBr tablet method) of the powder disappeared and the powder was same as the original (de-carbobutoxy) azo pigment.

Example 12

0.48 g of the azo compound (III-4) (E=$C_5H_9O_2$) prepared in Example 2 and 1.0 g of trifluoroacetic acid were reacted with 50 ml of o-dichlorobenzene for 4 hrs under a reflux temperature. The reactant gradually became blackish and a navy-blue material precipitated. At room temperature, the precipitate was filtered with a fluoro pore having a size of 0.1 micron and washed with 50 ml of tetrahydrofuran to prepare a raisin powder.

The absorption by saturated hydrocarbon observed at 2,980 $cm^{-1}$ and the absorption based on a stretching vibration of carbonate C=O observed at 1,760 $cm^{-1}$ in an infrared absorption spectrum (KBr tablet method) of the powder disappeared and the powder was same as the original azo pigment.

Example 13

0.48 g of the azo compound (III-2) (E=$C_5H_9O_2$) prepared in Example 3 and 1.0 g of trifluoroacetic acid were reacted with 50 ml of chlorobenzene for 5 hrs under a reflux temperature. The reactant gradually became blackish and a navy-blue material precipitated. At room temperature, the precipitate was filtered with a fluoro pore having a size of 0.1 micron and washed with 50 ml of tetrahydrofuran to prepare a raisin powder.

The absorption by saturated hydrocarbon observed at 2,980 $cm^{-1}$ and the absorption based on a stretching vibration of carbonate C=O observed at 1,760 $cm^{-1}$ in an infrared absorption spectrum (KBr tablet method) of the powder disappeared and the powder was same as the original azo pigment.

Example 14

0.52 g of the azo compound (III-3) (E=$C_8H_7O_2$) prepared in Example 4 and 2.0 g of acetic acid were reacted with 50 ml of toluene for 5 hrs at 80° C. The reactant gradually became blackish and a navy-blue material precipitated. At room temperature, the precipitate was filtered with a fluoro pore having a size of 0.1 micron and washed with 50 ml of tetrahydrofuran to prepare a raisin powder.

The absorption by saturated hydrocarbon observed at 2,980 $cm^{-1}$ and the absorption based on a stretching vibration of carbonate C=O observed at 1,760 $cm^{-1}$ in an infrared absorption spectrum (KBr tablet method) of the powder disappeared and the powder was same as the original azo pigment.

Example 15

1.18 g of the azo compound (IV-1) (E=$C_5H_9O_2$) prepared in Example 5 were reacted with 100 ml of o-xylene for 5 hrs under a reflux temperature. The reactant gradually became blackish and a navy-blue material precipitated. At room temperature, the precipitate was filtered with a fluoro pore having a size of 0.1 micron and washed with 50 ml of tetrahydrofuran to prepare a perse powder.

The absorption by saturated hydrocarbon observed at 2,980 $cm^{-1}$ and the absorption based on a stretching vibration of carbonate C=O observed at 1,760 $cm^{-1}$ in an infrared absorption spectrum (KBr tablet method) of the powder disappeared and the powder was same as the original azo pigment.

Example 16

0.53 g of the azo compound (V-1) (E=$C_5H_9O_2$) prepared in Example 6 and 1.0 g of trifluoroacetic acid were reacted with 50 ml of chlorobenzene for 5 hrs under a reflux temperature. The reactant gradually became blackish and a navy-blue material precipitated. At room temperature, the precipitate was filtered with a fluoro pore having a size of 0.1 micron and washed with 50 ml of tetrahydrofuran to prepare a raisin powder.

The absorption by saturated hydrocarbon observed at 2,980 cm$^{-1}$ and the absorption based on a stretching vibration of carbonate C=O observed at 1,760 cm$^{-1}$ in an infrared absorption spectrum (KBr tablet method) of the powder disappeared and the powder was same as the original azo pigment.

Example 17

0.50 g of the azo compound (VI-1) (E=$C_5H_9O_2$) prepared in Example 7 and 1.0 g of hydrochloric acid were reacted with 50 ml of cyclohexanone for 5 hrs under a reflux temperature. The reactant gradually became blackish and a navy-blue material precipitated. At room temperature, the precipitate was filtered with a fluoro pore having a size of 0.1 micron and washed with 50 ml of tetrahydrofuran to prepare a perse powder.

The absorption by saturated hydrocarbon observed at 2,980 cm$^{-1}$ and the absorption based on a stretching vibration of carbonate C=O observed at 1,760 cm$^{-1}$ in an infrared absorption spectrum (KBr tablet method) of the powder disappeared and the powder was same as the original azo pigment.

Example 18

0.53 g of the azo compound (VII-2) (E=$C_8H_7O_2$) prepared in Example 8 and 2.0 g of trifluoroacetic acid were reacted with 50 ml of N,N-dimethylformamide for 3 hrs under a reflux temperature. The reactant gradually became bluish and a navy-blue material precipitated. At room temperature, the precipitate was filtered with a fluoro pore having a size of 0.1 micron and washed with 50 ml of tetrahydrofuran to prepare a perse powder.

The absorption by saturated hydrocarbon observed at 2,980 cm$^{-1}$ and the absorption based on a stretching vibration of carbonate C=O observed at 1,760 cm$^{-1}$ in an infrared absorption spectrum (KBr tablet method) of the powder disappeared and the powder was same as the original azo pigment.

Example 19

0.46 g of the azo compound (VIII-5) (E=$C_5H_9O_2$) prepared in Example 9 and 1.0 g of trifluoroacetic acid were reacted with 50 ml of chlorobenzene for 3 hrs at 100° C. The reactant gradually became bluish and a navy-blue material precipitated. At room temperature, the precipitate was filtered with a fluoro pore having a size of 0.1 micron and washed with 50 ml of tetrahydrofuran to prepare a perse powder.

The absorption by saturated hydrocarbon observed at 2,980 cm$^{-1}$ and the absorption based on a stretching vibration of carbonate C=O observed at 1,760 cm$^{-1}$ in an infrared absorption spectrum (KBr tablet method) of the powder disappeared and the powder was same as the original azo pigment.

Example 20

0.32 g of the azo compound (X-1) (E=$C_5H_9O_2$) prepared in Example 10 and 1.0 g of trifluoroacetic acid were reacted with 50 ml of o-dichlorobenzene for 4 hrs under a reflux temperature. The reactant gradually became blackish and a navy-blue material precipitated. At room temperature, the precipitate was filtered with a fluoro pore having a size of 0.1 micron and washed with 50 ml of tetrahydrofuran to prepare a raisin powder.

The absorption by saturated hydrocarbon observed at 2,980 cm$^{-1}$ and the absorption based on a stretching vibration of carbonate C=O observed at 1,760 cm$^{-1}$ in an infrared absorption spectrum (KBr tablet method) of the powder disappeared and the powder was same as the original azo pigment.

Example 21

0.30 g of the azo compound (III-2) (E=$C_5H_9O_2$) prepared in Example 3 were placed in an egg-plant-shaped flask and reacted for 2 hrs at 170° C. The reactant gradually became black bluish and a raisin powder was prepared at room temperature.

The absorption by saturated hydrocarbon observed at 2,980 cm$^{-1}$ and the absorption based on a stretching vibration of carbonate C=O observed at 1,760 cm$^{-1}$ in an infrared absorption spectrum (KBr tablet method) of the powder disappeared and the powder was same as the original azo pigment.

Example 22

According to Example 5 in Japanese patent No. 3026645, an azo pigment was prepared. However, after the reaction, the reactant was not washed and purified with N,N-dimethylformamide and the azo pigment was prepared according to Example 3.

1.61 g of the azo compound (III-2) (E=H) and 4.3 g of (10 times mol) of pyrocarboxylic acid di-tert-butyl ester were dispersed in 50 ml of dehydrated pyridine and 200 ml of N,N-dimethylformamide to prepare a dispersion. After the dispersion was stirred for 15 min at room temperature, the dispersion was heated to have a temperature about 50° C. and further reacted for 2 hrs. The reactant gradually became reddish and a uniform solution was prepared. The solvents were removed therefrom at room temperature and about 100 ml of ethylacetate were added thereto to prepare a red powder.

The red powder was further purified by column chromatogram (silica gel/chloroform) and reacted according to Example 13 to prepare a raisin powder.

The absorption by saturated hydrocarbon observed at 2,980 cm$^{-1}$ and the absorption based on a stretching vibration of carbonate C=O observed at 1,760 cm$^{-1}$ in an infrared absorption spectrum (KBr tablet method) of the powder disappeared and the powder was same as the original azo pigment.

Application Example

The procedure for preparation of a multilayered electrophotographic photoreceptor in Application Example 2 of Japanese patent No. 3026645 was repeated except for using the azo pigment prepared in Example 22.

After the multilayered photoreceptor was negatively-charged by electrostatic copy paper tester SP428 from Kawaguchi Electric Works Co., Ltd. with a corona discharge at −6 KV for 20 sec, it was left in a dark space for 20 sec and the surface potential Vpo (V) thereof was measured. Next, the photoreceptor was irradiated by a tungsten lamp such that the surface thereof has an illuminance of 4.5 lux and a time (sec) until the Vpo became half due to light attenuation was measured to determine a half decay of light exposure E½ (lux·sec)

as a sensitivity thereof. The photoreceptor had a Vpo of −1,105 V and an E½ of 0.6 lux·sec, i.e., a high sensitivity.

Additional modifications and variations of the present invention are possible in light of the above teachings. It is therefore to be understood that within the scope of the appended claims the invention may be practiced other than as specifically described herein.

This document claims priority and contains subject matter related to Japanese Patent Applications Nos. 2007-172269 and 2007-235747, filed on Jun. 29, 2007 and Sep. 11, 2007, respectively, the entire contents of which are herein incorporated by reference.

What is claimed is:

1. An azo compound represented by the following formula (I):

$$A(E)n \qquad (I)$$

wherein A represents a residue of an azo compound, bonded with n pieces of E group through one or more heteroatom being N or O and forming a part of the residue A; E independently represents —C(=O)—O—R1 wherein R1 represents a substituted or an unsubstituted alkyl group having 4 to 10 carbon atoms, an alkenyl group, an alkynyl group, a cycloalkyl group, a cycloalkenyl group or an aralkyl group; and n represents an integer of from 1 to 10;

wherein the A is the residue of a compound having the following formula (II):

$$B—(N=N-Cp)m \qquad (II)$$

wherein B represents a main backbone of an azo compound; Cp represents a coupler component residue; and m is 2;

wherein the B has the following formula (VI):

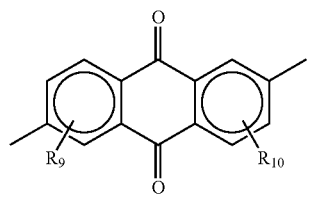

(VI)

wherein $R_9$ and $R_{10}$ independently represent a hydrogen atom, a halogen atom, a substituted or an unsubstituted alkyl group, a substituted or an unsubstituted alkoxy group, and a carboxyl group and its esters; and wherein the Cp represented by the following formula (6):

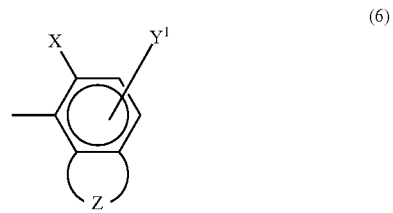

(6)

wherein X represents —OH, —N($R^1$)($R^2$) or —NHSO$_2$—$R^3$ wherein $R^1$ and $R^2$ independently represents a hydrogen atom or a substituted or an unsubstituted alkyl group, and $R^3$ represents a substituted or an unsubstituted alkyl group or a substituted or an unsubstituted aryl group; $Y^1$ represents a hydrogen atom, a halogen atom, a substituted or an unsubstituted alkyl group, a substituted or an unsubstituted alkoxy group, a carboxy group, a sulfone group, a substituted or an unsubstituted sulfamoyl group or —CON($R^4$)($Y^2$) wherein $R^4$ represents an alkyl group or its substituents, or a phenyl group or its substituents, and $Y^2$ represents a ring hydrocarbon group or its substituents, a heterocyclic group or its substituents, or —N=C($R^5$)($R^6$) wherein $R^5$ represents a ring hydrocarbon group or its substituents, a heterocyclic group or its substituents, or a styryl group or its substituents, $R^6$ represents a hydrogen atom, an alkyl group, or a phenyl group or its substituents, and alternatively $R^5$ and $R^6$ optionally form a ring with carbon atoms bonded therewith; and Z represents a ring hydrocarbon group or its substituents, or a heterocyclic group or its substituents.

* * * * *